(12) United States Patent
Breinlinger et al.

(10) Patent No.: US 9,617,145 B2
(45) Date of Patent: Apr. 11, 2017

(54) EXPORTING A SELECTED GROUP OF MICRO-OBJECTS FROM A MICRO-FLUIDIC DEVICE

(71) Applicant: Berkeley Lights, Inc., Emeryville, CA (US)

(72) Inventors: Keith J. Breinlinger, San Ramon, CA (US); Daniele Malleo, El Cerrito, CA (US); Gaetan L. Mathieu, Varennes (CA); J. Tanner Nevill, El Cerrito, CA (US); Alexander H. Slocum, Bow, NH (US); Mark P. White, San Francisco, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 181 days.

(21) Appl. No.: 14/520,510

(22) Filed: Oct. 22, 2014

(65) Prior Publication Data

US 2015/0151307 A1 Jun. 4, 2015

Related U.S. Application Data

(60) Provisional application No. 61/996,962, filed on Oct. 22, 2013, provisional application No. 61/996,973, (Continued)

(51) Int. Cl.
*B03C 7/02* (2006.01)
*B81B 7/02* (2006.01)
(Continued)

(52) U.S. Cl.
CPC ............... *B81B 7/02* (2013.01); *B03C 5/005* (2013.01); *B03C 5/026* (2013.01);
(Continued)

(58) Field of Classification Search
CPC ..... B03C 2201/26; B03C 5/005; B03C 5/026; B01L 2200/0668; B01L 2300/0636;
(Continued)

(56) References Cited

U.S. PATENT DOCUMENTS

| 7,612,355 B2 | 11/2009 | Wu et al. |
| 2003/0008364 A1 | 1/2003 | Wang |

(Continued)

FOREIGN PATENT DOCUMENTS

| EP | 1065378 A2 | 1/2001 |
| WO | 2012050981 A1 | 4/2012 |
| WO | 2012058637 A2 | 5/2012 |

OTHER PUBLICATIONS

International Bureau of WIPO, International Preliminary Report on Patentability for PCT/US2014/061787, May 6, 2016.
(Continued)

*Primary Examiner* — Jennifer Wecker
(74) *Attorney, Agent, or Firm* — Kenneth E. Horton; Kirton McConkie

(57) ABSTRACT

A group of micro-objects in a holding pen in a micro-fluidic device can be selected and moved to a staging area, from which the micro-objects can be exported from the micro-fluidic device. The micro-fluidic device can have a plurality of holding pens, and each holding pen can isolate micro-objects located in the holding pen from micro-objects located in the other holding pens or elsewhere in the micro-fluidic device. The selected group of micro-objects can comprise one or more biological cells, such as a clonal population of cells. Embodiments of the invention can thus select a particular group of clonal cells in a micro-fluidic device, move the clonal cells to a staging area, and export the clonal cells from the micro-fluidic device while maintaining the clonal nature of the exported group.

29 Claims, 17 Drawing Sheets

Related U.S. Application Data filed on Oct. 22, 2013, provisional application No. 62/058,658, filed on Oct. 1, 2014.

(51) Int. Cl.
    *B03C 5/00*     (2006.01)
    *B03C 5/02*     (2006.01)
    *G01N 33/00*     (2006.01)
    *G01N 27/447*     (2006.01)
    *B01L 3/00*     (2006.01)
    *G01N 33/50*     (2006.01)

(52) U.S. Cl.
CPC . *B01L 3/502761* (2013.01); *B01L 2200/0668* (2013.01); *B01L 2300/0636* (2013.01); *B01L 2300/087* (2013.01); *B01L 2300/0816* (2013.01); *B01L 2300/0819* (2013.01); *B01L 2300/0864* (2013.01); *B01L 2300/0877* (2013.01); *B01L 2400/0424* (2013.01); *B01L 2400/0454* (2013.01); *B01L 2400/086* (2013.01); *B03C 2201/26* (2013.01); *G01N 27/44791* (2013.01); *G01N 33/5023* (2013.01)

(58) Field of Classification Search
CPC ..... B01L 2300/0816; B01L 2300/0864; B01L 2300/087; B01L 2400/0454; B01L 3/502761; B81B 7/02; G01N 33/5023
See application file for complete search history.

(56) References Cited

U.S. PATENT DOCUMENTS

| | | |
|---|---|---|
| 2004/0072278 A1 | 4/2004 | Chou |
| 2007/0095669 A1 | 5/2007 | Lau |
| 2008/0302732 A1 | 12/2008 | Soh |
| 2010/0003666 A1 | 1/2010 | Lee et al. |
| 2010/0263599 A1 | 10/2010 | Yanik et al. |
| 2011/0117634 A1* | 5/2011 | Halamish ............... C12M 23/12 435/283.1 |
| 2011/0143964 A1 | 6/2011 | Zhou et al. |
| 2011/0262906 A1 | 10/2011 | Dimov et al. |
| 2013/0118905 A1* | 5/2013 | Morimoto ......... B01L 3/502761 204/643 |
| 2013/0190212 A1 | 7/2013 | Handique et al. |
| 2014/0116881 A1* | 5/2014 | Chapman .......... B01L 3/502761 204/451 |

OTHER PUBLICATIONS

International Bureau of WIPO, International Preliminary Report on Patentability for PCT/US2014/061848, May 6, 2016.

IEEE Transactions on Biomedical Circuits and Systems, vol. 3, No. 6, pp. 424-431 Dec. 2009.

Wang et al., Enhanced cell sorting and manipulation with combined optical tweezer and microfluidic chip technologies, Lab Chip 11:3656-62 (2011).

Fuchs et al., Electronic sorting and recovery of single live cells from microlitre sized samples, Lab Chip 6:121-126 (2006).

Iliescu et al., Continuous field-flow separation of particle populations in a dielectrophoretic chip with three dimensional electrodes, Applied Physics Letters 90:234104 (2007).

Hur et al., High-throughput size-based rare cell enrichment using microscale vortices, Biomicrofluidics 5:022206 (2011).

Chung et al., Imaging single-cell signaling dynamics with a deterministic high-density single-cell trap array, Anal. Chem. 83(18):7044-7052 (2011).

* cited by examiner

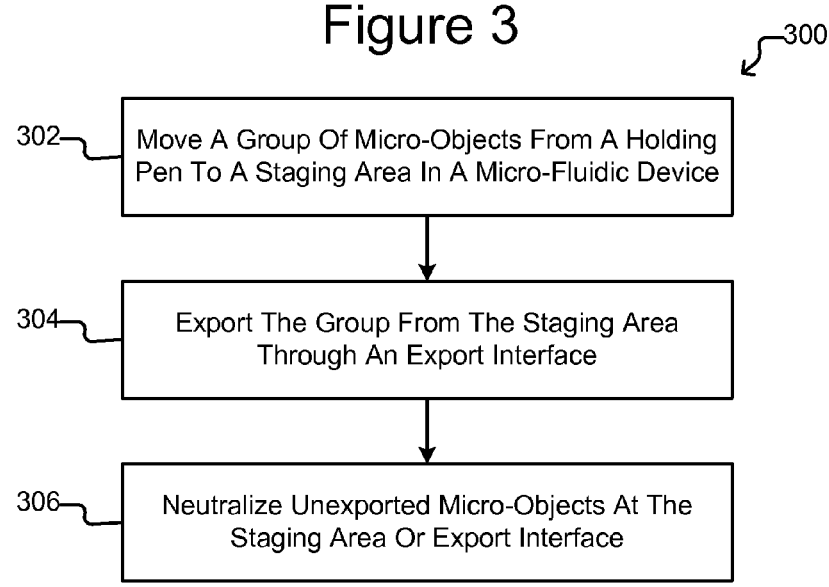
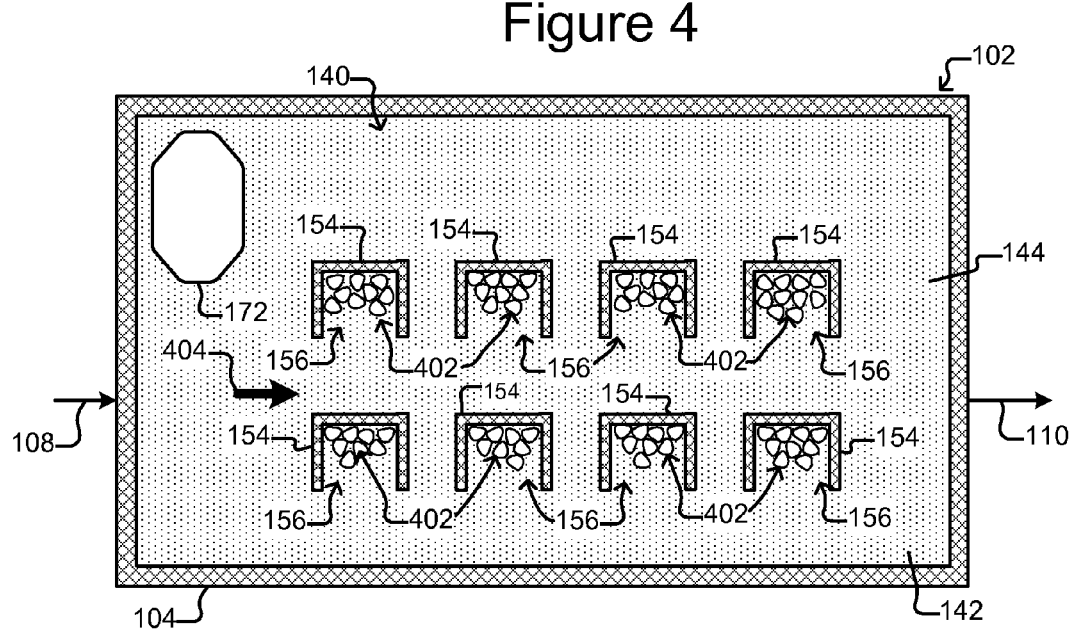

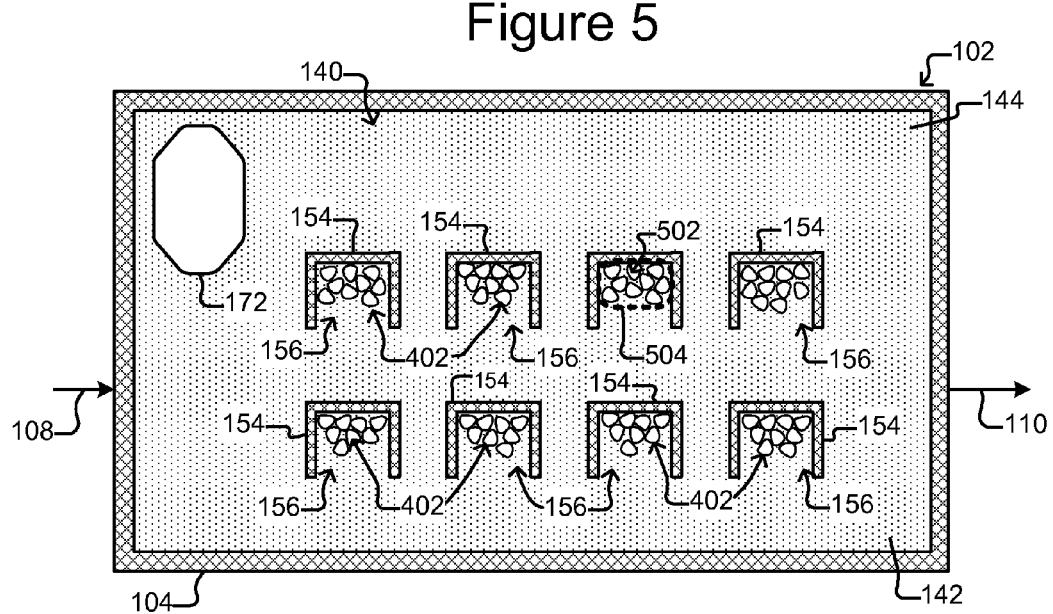
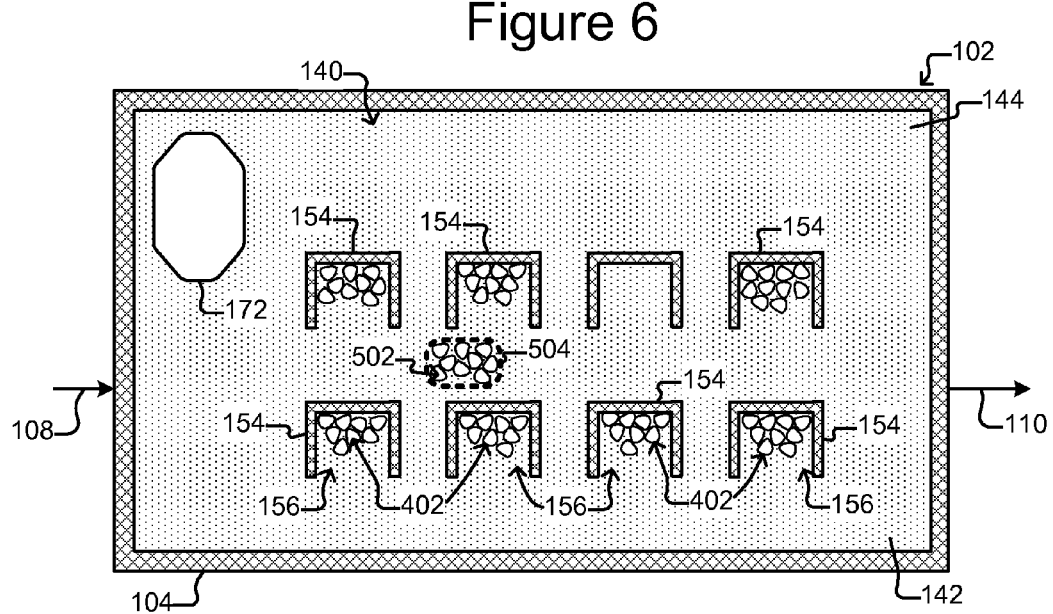

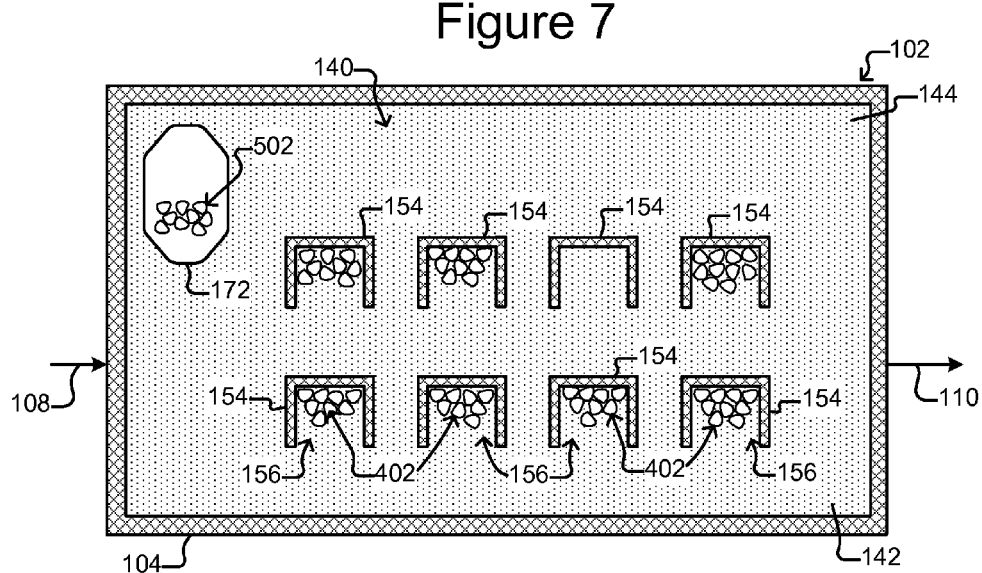
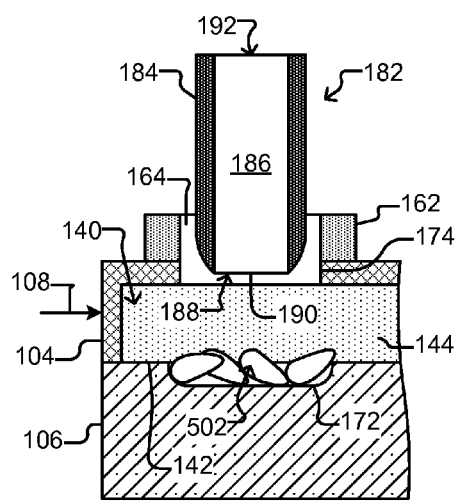 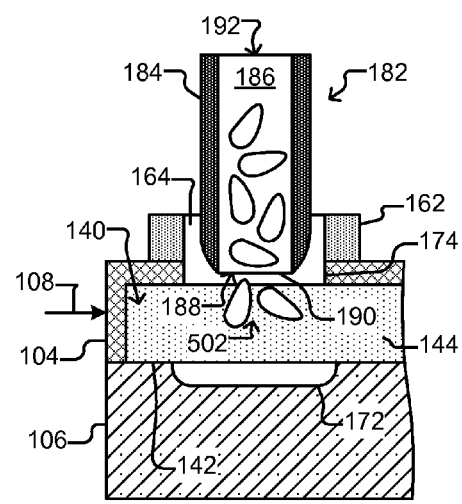

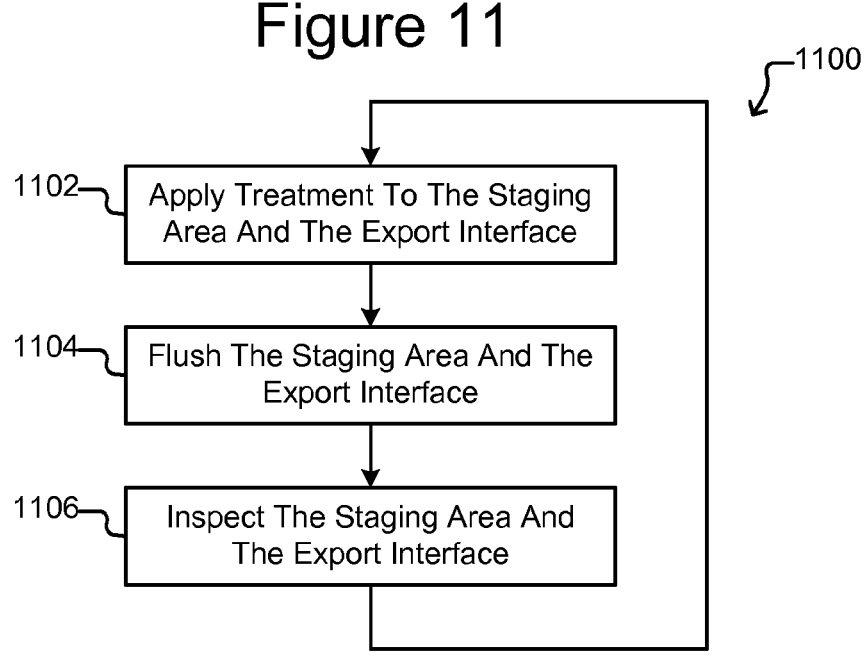
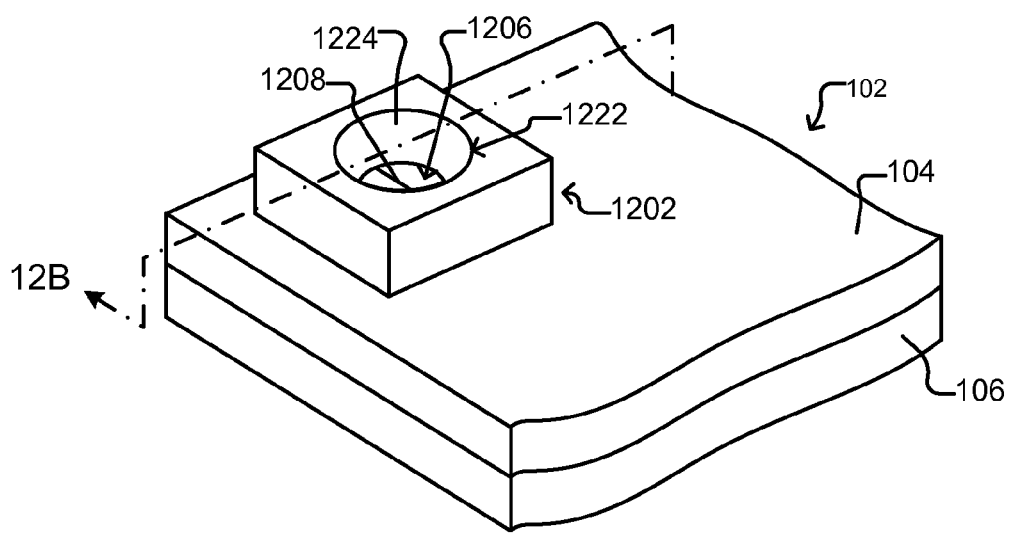

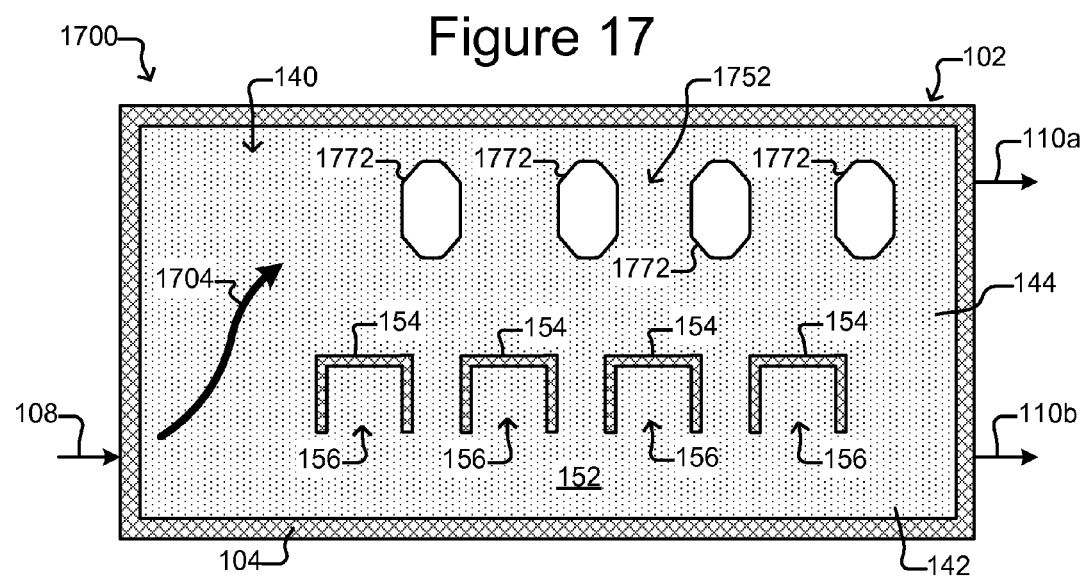
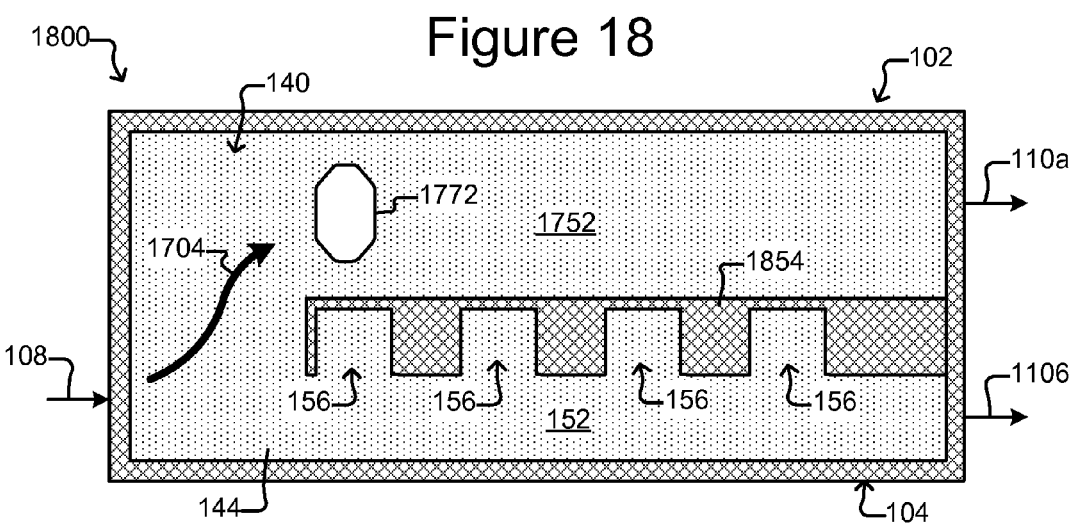

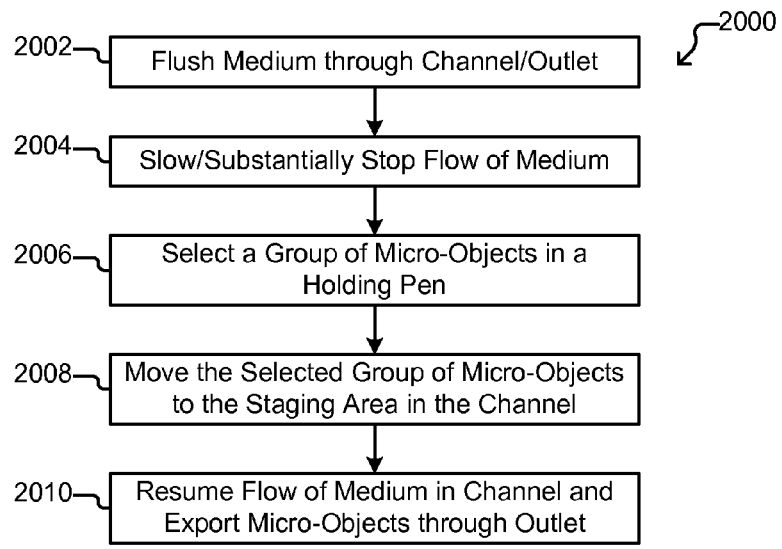
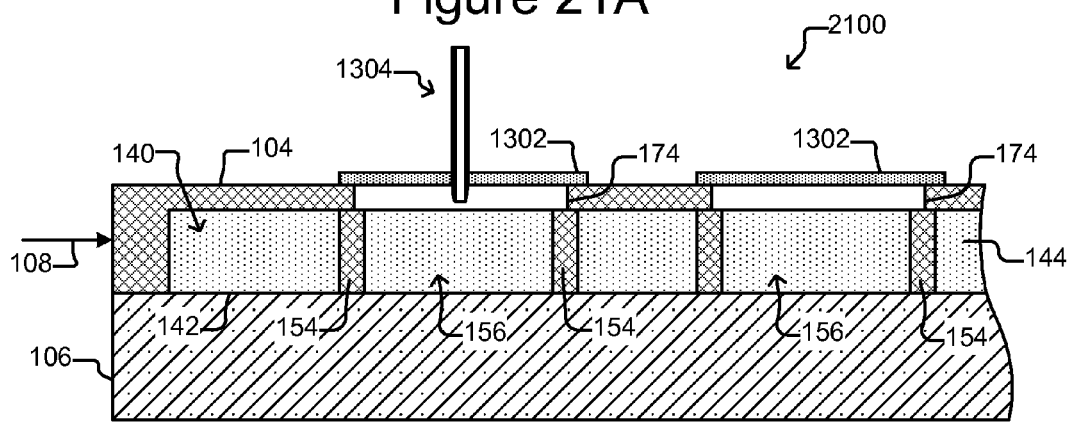

EXPORTING A SELECTED GROUP OF MICRO-OBJECTS FROM A MICRO-FLUIDIC DEVICE

CROSS REFERENCE TO RELATED APPLICATION(S)

The present application is a non-provisional of (and thus claims the benefit of and/or priority to) U.S. provisional patent application Ser. No. 61/996,962. Provisional application Ser. No. 61/996,962 was originally filed on Oct. 22, 2013 as a utility patent application, and assigned Ser. No. 14/060,237, but was subsequently converted to a U.S. provisional patent application in response to a Petition filed Oct. 17, 2014, which was granted Nov. 4, 2014. The present application also claims the benefit of and/or priority to US converted provisional patent application Ser. No. 61/996,969. Provisional application Ser. No. 61/996,969 was originally filed on Oct. 22, 2013 as a utility patent application and assigned Ser. No. 14/060,321, but was subsequently converted to a U.S. provisional patent application in response to a Petition filed Oct. 7, 2014, which was granted Oct. 9, 2014. This application also claims the benefit of U.S. provisional patent application Ser. No. 62/058,658, filed Oct. 1, 2014.

BACKGROUND

In biosciences and related fields, it can be useful to export selected elements from a micro-fluidic device. Some embodiments of the present invention include apparatuses and processes for selecting a group of micro-objects in a particular holding pen in a micro-fluidic device and exporting the selected group from the micro-fluidic device.

SUMMARY

In some embodiments, the invention provides a process of exporting micro-objects from a micro-fluidic device. The process can include selecting a group of micro-objects located in a holding pen located inside an enclosure of the micro-fluidic device. The holding pen can be one of a plurality of holding pens located inside the enclosure. The process can further include moving the selected group of micro-objects to a staging area inside the enclosure, and exporting the selected group of micro-objects from said staging area, through a passage in the enclosure, to a location outside of said enclosure. In certain embodiments, each holding pen in the enclosure includes an isolation region configured to hold a plurality of micro-objects. In certain embodiments, moving the group of micro-objects includes isolating the group of micro-objects from all other micro-objects disposed within the micro-fluidic device.

In certain embodiments, one or more (or all) of the micro-object in the selected group is a biological cell. In certain embodiments, the selected group of micro-objects is a single biological cell, such as an immunological cell, a cancer cell, a transformed cell, a stem cell, or the like. In other embodiments, the selected group of micro-objects is a plurality of cells, such as a clonal population of biological cells.

In certain embodiments, selecting the group of micro-objects includes determining that said group of micro-objects has a particular activity or physical characteristic.

In certain embodiments, selecting the group of micro-objects includes directing a pattern of light into the micro-fluidic device such that the pattern of light surrounds the micro-objects of the selected group and activates DEP forces that trap the micro-objects of the selected group. In certain related embodiments, moving the selected group of micro-objects includes moving the pattern of light that surrounds the group to the staging area such that, as the pattern of light moves to the staging area, the micro-objects of the selected group remain trapped by the DEP forces activated by the pattern of light.

In certain embodiments, the staging area is located in a channel defined by the enclosure of the micro-fluidic device. For example, the staging area can be adjacent to an opening from the holding pen that contains the selected group of micro-objects into the channel. In other embodiments, the staging area is located within the holding pen that contains the selected group of micro-objects. In certain related embodiments, moving the selected group of micro-objects to the staging area includes allowing gravity to attract the group of micro-objects to the staging area.

In certain embodiments, exporting the selected group of micro-objects includes drawing the micro-objects of the selected group from the staging area, through the passage in the enclosure. In certain embodiments, an export device is used to draw the micro-objects of the selected group through a proximal end of the export device and thereby through the passage in the enclosure. In certain embodiments, drawing the micro-objects of the selected group through the passage in the enclosure includes generating a pressure differential that draws the micro-objects of the group into the opening at the proximal end of the export device. In certain embodiments, the export device is inserted into an export interface disposed over the passage in the enclosure before the selected group of micro-objects is exported. In certain embodiments, inserting the export device into the export interface places the opening at the proximal end of the export device adjacent to the passage in the enclosure.

In certain embodiments, the micro-fluidic device includes an export interface that has a self-closing cover disposed over and covering the passage in the enclosure. In certain embodiments, an export device can be inserted into such an export interface by pressing the proximal end of the export device against a separation in the self-closing cover and moving the proximal end of the export device to a position adjacent to the passage in the enclosure.

In certain embodiments, the micro-fluidic device includes an export interface that has a self-healing cover disposed over and covering the passage in the enclosure. In certain embodiments, an export device can be inserted into such an export interface by piercing the self-healing cover with the proximal end of the export device and positioning the proximal end of the export device adjacent to the passage in the enclosure.

In certain embodiments, the selected group of micro-objects is exported in a medium or other solution having a volume of 1 µL or less. In other embodiments, the selected group of micro-objects is exported in a medium or other solution having a volume of 5 µL, 10 µL, 25 µL, 50 µL, or more.

In certain embodiments, after the selected group of micro-objects is exported from the micro-fluidic device, the staging area, the export interface, the export device, or any combination thereof is inspected for micro-objects of the selected group that failed to get exported. In certain embodiments, micro-objects that failed to get exported are removed from the staging area, the export interface, and/or the export device. The micro-objects that failed to get exported can be removed, for example, by flushing and/or neutralizing the staging area, the export interface, and/or the export device.

In certain embodiments, the enclosure of the micro-fluidic device includes a first passage and a second passage. In certain embodiments, the first passage is located adjacent to a first end of the staging area and the second passage is located adjacent to a second end of the staging area. In some embodiments, the staging area has an elongated shape. In certain related embodiments, moving the selected group of micro-objects includes moving the group to a position in the staging area that is located at the first end, at the second end, or between the first end and the second end of the staging area. In certain related embodiments, exporting the selected group of micro-objects includes flowing a liquid from a first export device through the first passage in the enclosure toward the first end of the staging area, and thereby generating a flow from the first end of the staging area to the second end of the staging area. In other related embodiments, exporting the selected group of micro-objects includes drawing the micro-objects of the selected group from the second end of the staging area through the second passage in the enclosure, into an opening at a proximal end of a second export device located adjacent to the second passage.

In some embodiments, a process of exporting micro-objects from a micro-fluidic device can include creating a flow of liquid medium in an enclosure of the micro-fluidic device directly to an outlet from the enclosure for the medium. In certain embodiments, the flow of liquid medium is in a channel located within the enclosure. The process can also include selecting a group of micro-objects in a holding pen inside the enclosure, and moving the selected group from the holding pen into the flow path of the liquid medium. In certain embodiments, the flow of liquid medium is maintained sufficiently for the flow to sweep the selected group to the outlet and out of the enclosure through the outlet. In certain embodiments, the flow of liquid medium is slowed or stopped while the selected group is moved from the holding pen into the flow path.

In some embodiments, the invention provides a micro-fluidic apparatus. The micro-fluidic apparatus can include an enclosure configured to contain a liquid medium and a passage through the enclosure. The micro-fluidic apparatus can further include a channel disposed inside the enclosure and at least one holding pen which opens off of the channel. In certain embodiments, the micro-fluidic device includes a plurality of holding pens which open off of the channel. Each holding pen can be configured to hold a group of micro-objects. In certain embodiments, each holding pen is configured to isolate the group of micro-objects from micro-objects in other holding pens in the micro-fluidic device. In certain embodiments, each holding pen includes an isolation region.

In certain embodiments, the micro-fluidic apparatus includes an export interface. For example, the export interface can be disposed on the enclosure adjacent to the passage through the enclosure. In certain embodiments, the export interface comprises a cover that covers entirely the passage through the enclosure. In certain embodiments, the export interface is configured to interface with an export device such that an opening in a first (or proximal) end of the export device is located adjacent to the passage through the enclosure.

In certain embodiments, the cover of the export interface includes a separation that divides the cover into contiguous flaps. In certain embodiments, the flaps are biased to contact one another and thereby cover entirely the passage through the enclosure. In certain embodiments, the flaps of the cover are sufficiently flexible to move apart and form an opening that can receive the first end of the export device when the first end of the export device is pressed against the separation that divides the cover into contiguous flaps. In other embodiments, the cover of the export interface includes a self-healing material that can be pierced by an export device. In certain embodiments, such piercing forms a hole for receiving said export device, but the hole can self-heal and thereby close when the export device is removed from the cover.

In certain embodiments, the enclosure of the micro-fluidic device includes at least one staging area. In certain embodiments, the at least one staging area is located adjacent to the passage through said enclosure. In certain embodiments, the staging area is located in the channel. In certain embodiments, the enclosure comprises a plurality of staging areas. In certain embodiments, each holding pen in the micro-fluidic device includes a staging area.

In some embodiments, the invention provides a system. The system can include a micro-fluidic device and a means for trapping and moving a group of micro-objects located within the micro-fluidic device. The micro-fluidic device can be any device described herein. In certain embodiments, the means for trapping and moving the group of micro-objects is suitable for trapping a group of micro-objects located in a holding pen within the micro-fluidic device and moving the trapped group of micro-objects to a staging area.

These and other aspects and advantages of the methods, systems, and devices of the invention will be set forth or will become more fully apparent in the description that follows and in the appended claims. The features and advantages may be realized and obtained by means of the instruments and combinations particularly pointed out in the appended Examples and claims. Furthermore, the aspects and advantages of the described systems, devices, and methods may be learned by the practice or will be obvious from the description, as set forth hereinafter.

BRIEF DESCRIPTION OF THE DRAWINGS

FIG. 3 is an example of a process for exporting a group of micro-objects from a micro-fluidic device.

FIG. 4 shows an example of groups of micro-objects in holding pens in the micro-fluidic device of FIGS. 1A-1C.

FIG. 5 illustrates an example of selecting and trapping a group of micro-objects in one of the holding pens.

FIG. 6 shows an example of moving the trapped group of micro-objects from the holding pen toward a staging area in the micro-fluidic device.

FIG. 7 shows the group of micro-objects in the staging area.

FIG. 8 illustrates an example of an export device inserted into an export interface of the micro-fluidic device of FIGS. 1A-1C.

FIG. 9 shows an example of the micro-objects being drawn from the staging area into the export device.

FIG. 11 is an example process for neutralizing the staging area and export interface of un-exported micro-objects.

FIG. 12A is a partial, perspective view of the micro-fluidic device of FIGS. 1A-1C with an embodiment of the export interface that includes a self-closing cover.

FIG. 17 is a top, cross-sectional view of a micro-fluidic device comprising holding pens and multiple staging areas in a flow path in the device.

FIG. 18 is a top, cross-sectional view of a micro-fluidic device comprising holding pens and a staging area, with the holding pens opening from a channel that is separated by a continuous barrier from the flow path in which the staging area is located.

FIG. 20 illustrates an example of a process for exporting micro-objects from the device of FIGS. 19A-19B.

FIG. 21A is a partial, side, cross-sectional view of a micro-fluidic device in which export interfaces can be located directly adjacent to the holding pens.

DETAILED DESCRIPTION OF EXEMPLARY EMBODIMENTS

Figure 1A:
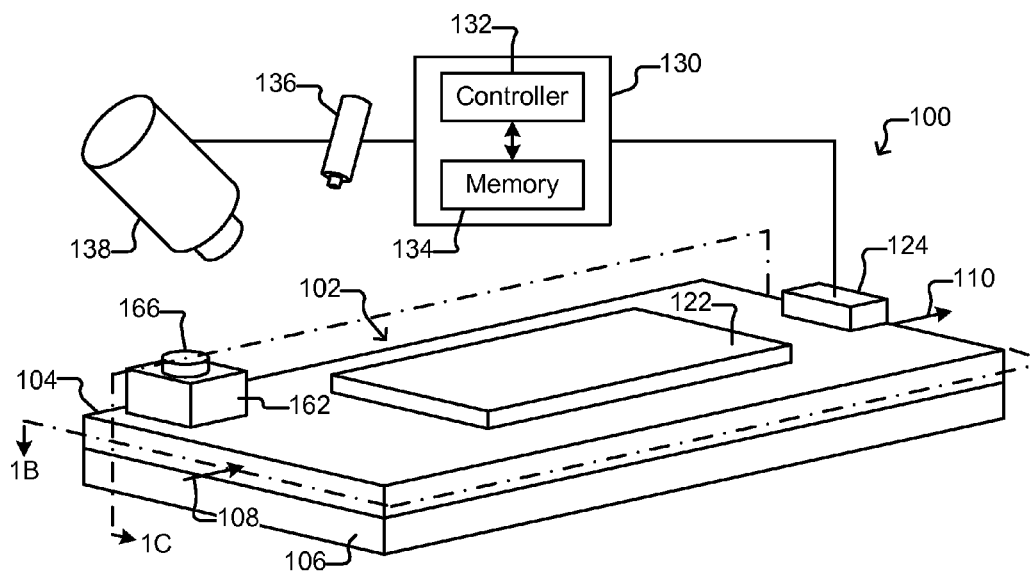
FIG. 1A is a perspective view of a micro-fluidic device.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion for clarity. In addition, as the terms "on," "attached to," or "coupled to" are used herein, one element (e.g., a material, a layer, a substrate, etc.) can be "on," "attached to," or "coupled to" another element regardless of whether the one element is directly on, attached, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. The term "ones" means more than one.

The term "aspirate" as used with respect to a micro-object means to move the micro-object utilizing a pressure differential, and an "aspirator" is a pressure differential generating device.

As used herein, the term "micro-object" can encompass one or more of the following: inanimate micro-objects such as microparticles, microbeads (e.g., polystyrene beads, Luminex™ beads, or the like), magnetic beads, microrods, microwires, quantum dots, and the like; biological micro-objects such as cells (e.g., embryos, oocytes, sperms, cells dissociated from a tissue, blood cells, hybridomas, cultured cells, cells from a cell line, cancer cells, infected cells, transfected and/or transformed cells, reporter cells, and the like), liposomes (e.g, synthetic or derived from membrane preparations), lipid nanorafts, and the like; or a combination of inanimate micro-objects and biological micro-objects (e.g., microbeads attached to cells, liposome-coated microbeads, liposome-coated magnetic beads, or the like). Lipid nanorafts have been described, e.g., in Ritchie et al. (2009) "Reconstitution of Membrane Proteins in Phospholipid Bilayer Nanodiscs," Methods Enzymol., 464:211-231.

The term "flow," as used herein with reference to a liquid, refers to bulk movement of the liquid primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a liquid that is less than the rate of diffusion of components of a material (e.g., an analyte of interest) into or within the liquid. The rate of diffusion of components of such a material can depend on, for example, temperature, the size of the components, and the strength of interactions between the components and the fluidic medium.

As used herein in reference to a fluidic medium, "diffuse" and "diffusion" refer to thermodynamic movement of a component of the fluidic medium down a concentration gradient.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic device or apparatus of the invention can comprise "swept" regions and "unswept" regions. An unswept region can be fluidically connected to a swept region, provided the fluidic connections are structured to enable diffusion but substantially no flow of media between the swept region and the unswept region. The microfluidic apparatus can thus be structured to substantially isolate an unswept region from a flow of medium in a swept region, while enabling substantially only diffusive fluidic communication between the swept region and the unswept region.

"Sterilizing" a biological cell means rendering the cell unable to reproduce.

As used herein, a "group" of micro-objects can be a single micro-object or a plurality of micro-objects. The group of micro-objects can be a clonal group of biological cells (e.g., one cell, a plurality of cells, or all of the cells from a clonal colony). A colony of biological cells is "clonal" if all of the living cells in the colony that are capable of reproducing are daughter cells derived from a single parent cell. "Clonal cells" are cells of the same clonal colony.

In some embodiments of the invention, a group of micro-objects can be captured from a selected holding pen in a micro-fluidic device and moved from the holding pen to a staging area, where the micro-objects of the group can be exported from the micro-fluidic device. The micro-objects can be biological cells. Each holding pen can isolate biological cells in the holding pen from biological cells in others of the holding pens (e.g., by having the biological cells located in an isolation region of the holding pen). The micro-objects captured from the selected holding pen can be clonal cells, and embodiments of the invention can select a particular group of clonal cells in a micro-fluidic device, move the clonal cells to a staging area, and export the clonal cells from the micro-fluidic device while maintaining the clonal nature of the group.

FIGS. 1A-1D illustrate an example of a micro-fluidic device 100 comprising holding pens 156, a selector 122, and an export interface 162. As will be seen, the selector 122 can select and move micro-objects (not shown) from any of the pens 156 to a staging area 172 inside an enclosure 102 of the device 100, and the export interface 162 provides an interface into the enclosure 102 for an external export device 182 that can export the micro-objects (not shown) from the staging area 172.

As shown in FIGS. 1A-1D, the micro-fluidic device 100 can comprise an enclosure 102, a selector 122, a flow controller 124, and an export interface 162 for an external export device 182. As also shown, the micro-fluidic device 100 can include auxiliary elements such as a control module 130, a source of electromagnetic radiation 136 (hereinafter an EM source 136), a detector 138, and/or the like.

The enclosure 102 can define a flow region 140 and hold a liquid medium 144. The enclosure 102 can comprise, for example, a micro-fluidic structure 104 disposed on a base (e.g., a substrate) 106. The micro-fluidic structure 104 can comprise a flexible material, such as rubber, plastic, an elastomer, silicone (e.g., patternable silicone), polydimethylsiloxane ("PDMS"), or the like, which can be gas permeable. Other examples of materials that can compose microfluidic structure 104 include molded glass, an etchable material such as silicon, photo-resist (e.g., SU8), or the like. In some embodiments, such materials—and thus the microfluidic structure 104—can be rigid and/or substantially impermeable to gas. Regardless, the microfluidic structure 104 can be disposed on the base 106. The base 106 can comprise one or more substrates. Although illustrated as a single structure, the base 106 can comprise multiple interconnected structures such as multiple substrates. The microfluidic structure 104 can likewise comprise multiple structures, which can be interconnected. For example, the microfluidic structure 104 can additionally comprise a cover (not shown) made from material that is the same as or different than the other material in the structure.

Figure 1B:
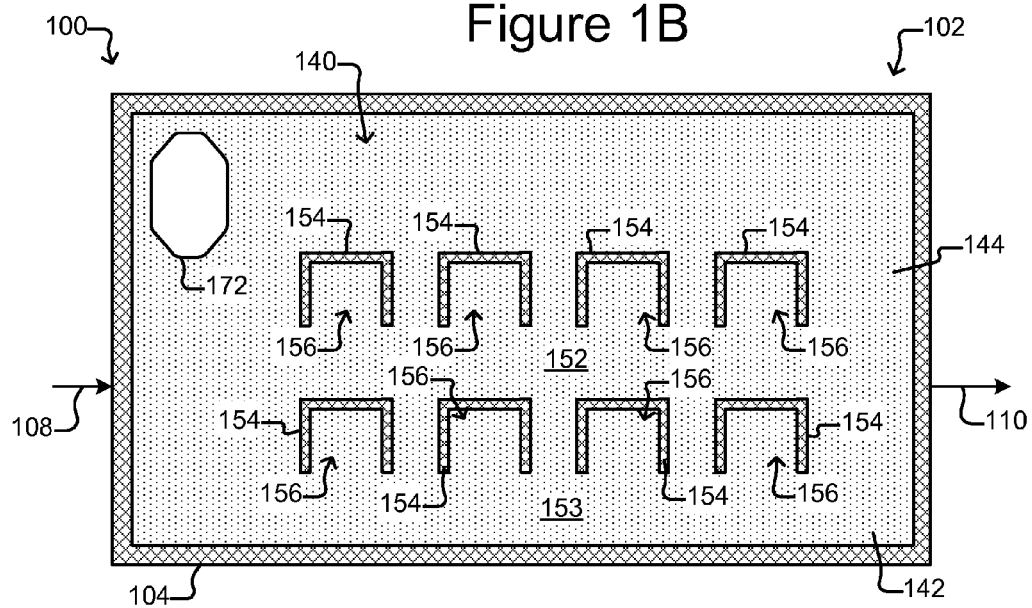
FIG. 1B is a top, cross-sectional view of the micro-fluidic device of FIG. 1A.
Figure 1C:
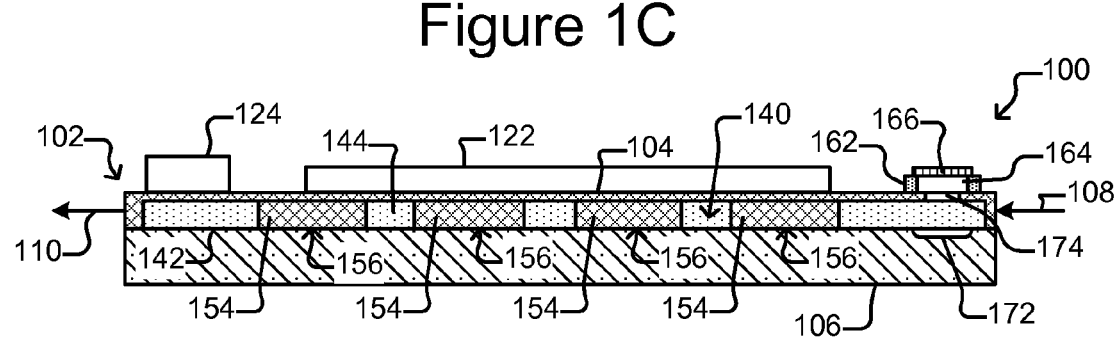
FIG. 1C is a side, cross-sectional view of the micro-fluidic device of FIG. 1A.

The micro-fluidic structure 104 and the base 106 can define a micro-fluidic flow region 140. Although one flow region 140 is shown in FIGS. 1A-1C, the micro-fluidic structure 104 and the base 106 can define multiple flow regions for the medium 144. The flow region 140 can comprise channels (152, 153 in FIG. 1B) and chambers, which can be interconnected to form micro-fluidic circuits. FIGS. 1B and 1C illustrate an inner surface 142 of the flow region 140 on which the medium 144 can be disposed as even (e.g., flat) and featureless. The inner surface 142, however, can alternatively be uneven (e.g., not flat) and comprise features such as electric terminals (not shown).

As shown, the enclosure 102 can comprise one or more inlets 108 through which medium 144 can be input into the flow region 140. An inlet 108 can be, for example, an input port, an opening, a valve, another channel, fluidic connectors, a tube, a fluid pump (e.g., a positive displacement syringe pump), or the like. The enclosure 102 can also comprise one or more outlets 110 through which the medium 144 can be removed from the flow region 140. An outlet 110 can be, for example, an output port, an opening, a valve, a channel, fluidic connectors, a tube, a pump, or the like. As another example, the outlet 110 can comprise a droplet outputting mechanism such as any of the outputting mechanisms disclosed in U.S. patent application Ser. No. 13/856,781 filed Apr. 4, 2013. All or part of the enclosure 102 can be gas permeable to allow gas (e.g., ambient air) to enter and exit the flow region 140. For enclosures that comprise more than one flow region 140, each flow region 140 can be associated with one or more inlets 108 and one or more outlets 110 for respectively inputting and removing medium 144 from the flow region 140.

As shown in FIGS. 1B and 1C, holding pens 156 can be disposed in the flow region 140. For example, each holding pen 156 can comprise a barrier 154 disposed on an interior surface 142 of the enclosure 102. There can be many such holding pens 156 in the flow region 140 disposed in any pattern, and the holding pens 156 can be any of many different sizes and shapes. For example, the holding pens 156 can comprise a structure as described in U.S. Provisional Application Ser. No. 62/058,658, filed Oct. 1, 2014. Thus, for example, the holding pens 156 can include a connection region (not shown) and an isolation region (not shown). As shown in FIG. 1B openings of the holding pens 156 can be disposed adjacent to a channel 152, 153, which can be a conduit for medium 144 flowing past the openings of more than one pen 156. The opening of each holding pen 156 can allow for the natural exchange of liquid medium 144 flowing in a channel 152, 153 but each holding pen 156 can otherwise be sufficiently enclosed to prevent micro-objects (not shown), such as biological cells, in any one pen 156 from mixing with micro-objects in any other pen 156. Although eight pens 156 and two channels 152, 153 are shown, there can be more or fewer. For example, there can be a single channel fluidically connected with 100, 250, 500, 1000, 2500, 5000, 10000, 25000, 50000, 100000, or more holding pens.

Medium 144 can be flowed in channels 152, 153 past openings in the holding pens 156. The flow of medium 144 in channels 152, 153 can, for example, provide nutrients to biological micro-objects (not shown) in the holding pens 156. The flow of medium 144 in channels 152, 153 can also provide for the removal of waste from the holding pens 156. For holding pens 156 that comprise an isolation region, exchange of nutrients and waste between the isolation regions and the channels 152, 153 can occur substantially only by diffusion.

Figure 1D:
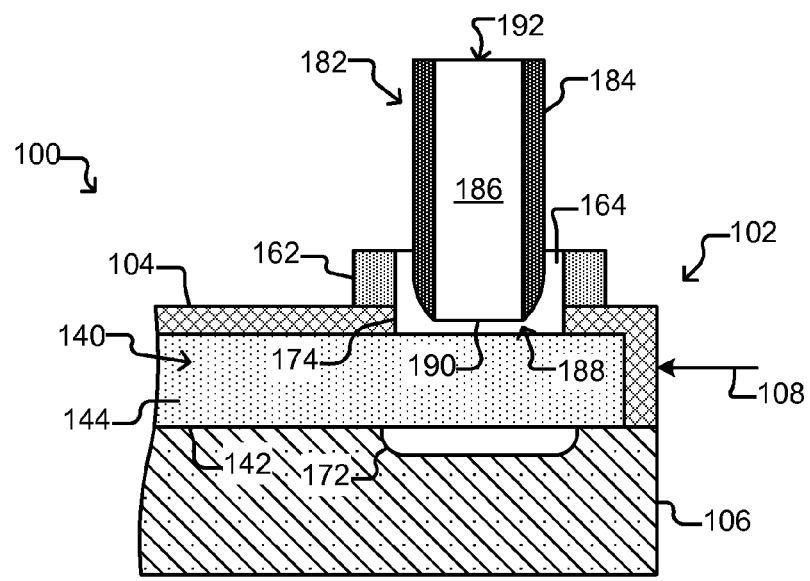
FIG. 1D is a partial, side, cross-sectional view of the micro-fluidic device of FIG. 1A illustrating insertion of an export device into an export interface.

As also shown, there can be a staging area 172 in the flow region 140 and thus inside the enclosure 102. The staging area 172 can be simply an area on an interior surface 142 of the enclosure 102, which can be marked or unmarked. Alternatively, the staging area 172 can comprise a structure in the flow region 140 such as a depression into the surface 142 (as shown in FIGS. 1B-1D), a platform (not shown) extending out of the surface 142, barriers (not shown) (e.g., similar to barriers 154), chambers, or the like. Regardless, as shown in FIG. 1D, the staging area 172 can be disposed adjacent to (e.g., across the flow region 140 from) a passage 174 through the enclosure 102 and into the flow region 140. The passage 174 can be from outside the enclosure 102 to inside the enclosure 102. The passage 174 can be, for example, a hole in the enclosure 102.

The export interface 162 can provide an interface to the passage 174 into the enclosure 102 for an external export device 182, which can be a device that is external to the enclosure 102. As shown in FIG. 1C, the export interface 162 can be disposed on the enclosure 102 adjacent to (e.g., over and/or within) the passage 174. The export interface 162 can comprise an opening 164 to the passage 174. The export interface 162 can further comprise a cover 166 over the opening 164. The cover 166 can be removable or otherwise breachable by the export device 182, which can be inserted into the opening 164 in the export interface 162 to engage the passage 174 into the enclosure 102. Although shown as distinct entities, the export interface 162 and the micro-fluidic structure 104 can be integrally formed of the same material and thus be portions of one physical entity.

The export interface 162 can comprise, for example, a flexible material such as polystyrene or any of the materials discussed above with respect to the micro-fluidic structure 104. Alternatively, the export interface 162 can comprise a hard or stiff material or a combination of flexible and hard or stiff materials. Examples of the cover 166 include a cover that can be attached to and detached from the enclosure 102, a cork like structure (not shown) that can be inserted into the opening 164 but is smaller than the passage 174, or the like. As will be seen in FIGS. 12A-13B, other examples of the cover 166 include a self-closing cover 1206 that can be pushed open by the export device 182 and an export interface 1302 in the form of a pierceable, self-healing structure.

As shown in FIG. 1D, the export device 182 can be a hollow tube-like structure. For example, the export device 182 can comprise a tubular housing 184 that defines an interior passage 186 from a first end 188 to an opposite second end 192. With the cover 166 of the export interface 162 removed, the export device 182 can be inserted into the opening 164 in the interface 162 such that the first end 188 is brought into proximity or contact with the enclosure passage 174. An opening 190 at the first end 188 of the export device 182 can thus be placed adjacent to the passage 174 into the enclosure 102.

In some embodiments, the export device 182 can be a pressure differential generating device (e.g., an aspirator, a positive displacement syringe pump, an air displacement pump, a peristaltic pump, or the like). For example, the export device 182 can be connectable to a source capable of generating a pressure differential (not shown), which can generate a pressure differential from the first end 188 to the second end 192 of the export device 182. The export device 182 can thus be configured to draw micro-objects (not shown) from the staging area 172 through the passage 174 into the opening 190 in its first end 188 through the internal passage 186 to the second end 192, where the micro-objects (not shown) can be collected or otherwise disposed of. Examples of the export device 182 include a pipette, a tube, a hollow needle such as a hypodermic needle, combination thereof or the like. The internal passage 186 of the export device can have a diameter of about 5 μm to 300 μm (e.g., about 25 to 300 μm, about 50 to 300 μm, about 75 to 300 μm, about 100 to 300 μm, about 100 to 250 μm, about 100 to 200 μm, about 100 to 150 μm, about 150 to 200 μm, or any other diameter or range defined by one or more of the foregoing endpoints).

The export device 182 can further comprise a sensor (not shown) capable of detecting micro-objects that pass through the export device. The sensor can be located proximal to the export interface 162. Alternatively, the sensor can be located distal to the export interface 162 (e.g., at the distal end of the export device 182). The sensor can be, for example, an imaging device, such as a camera (e.g., a digital camera) or a photosensor (e.g., a charge coupled device or a complementary metal-oxide semiconductor imager). Alternatively, the sensor can be an electrical device, such as a device that detects changes in complex impedance when micro-objects pass by.

The selector 122 can be configured to create selectively electrokinetic forces on micro-objects (not shown) in the medium 144. For example, the selector 122 can be configured to selectively activate (e.g., turn on) and deactivate (e.g., turn off) electrodes at the inner surface 142 of the flow region 140. The electrodes can create forces in the medium 144 that attract or repel micro-objects (not shown) in the medium 144, and the selector 122 can thus select and move one or more micro-objects in the medium 144. The electrodes can be, for example, dielectrophoresis (DEP) electrodes.

For example, the selector 122 can comprise one or more dielectrophoresis electrode devices, optical (e.g., laser) tweezers devices, and/or one or more optoelectronic tweezers (OET) devices (e.g., as disclosed in U.S. Pat. No. 7,612,355 (which is incorporated in its entirety by reference herein) or U.S. patent application Ser. No. 14/051,004 (which is also incorporated in its entirety by reference herein). As yet another example, the selector 122 can include one or more devices (not shown) for moving a droplet of the medium 144 in which one or more of the micro-objects are suspended. Such devices (not shown) can include electrowetting devices such as optoelectronic wetting (OEW) devices (e.g., as disclosed in U.S. Pat. No. 6,958,132) or other electrowetting devices. The selector 122 can thus be characterized as a DEP device in some embodiments.

Figure 2A:
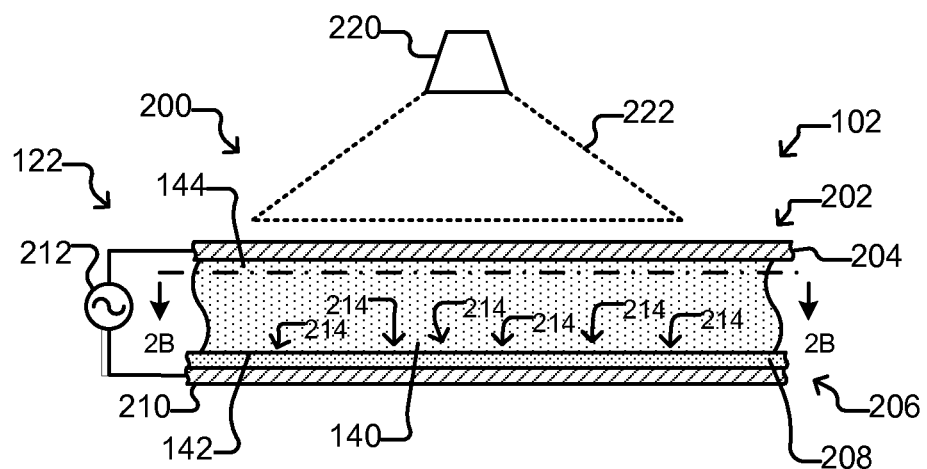
FIG. 2A is a partial side, cross-sectional view of the micro-fluidic device of FIGS. 1A-1C absent the holding pens (for ease of illustration) in which the selector is configured as a dielectrophoresis (DEP) device.
Figure 2B:
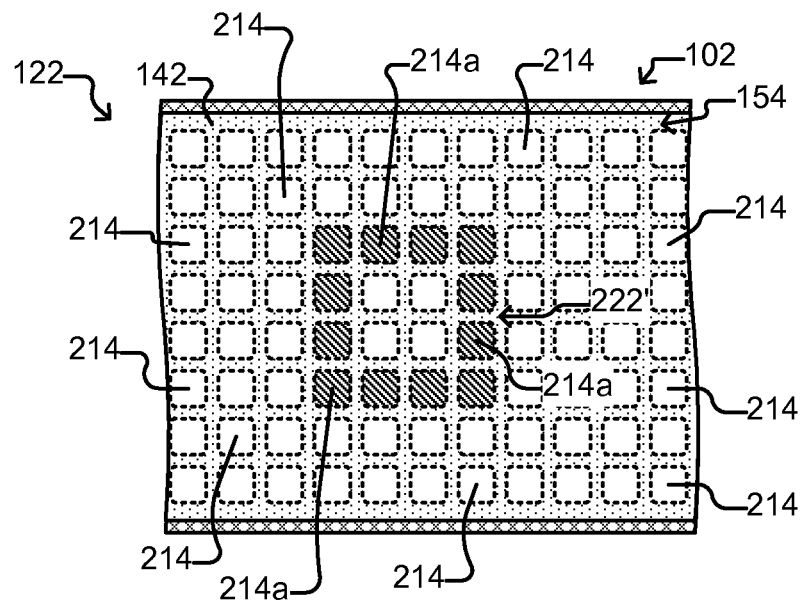
FIG. 2B is a partial top, cross-section view of FIG. 2A.

FIGS. 2A and 2B illustrate an example in which the selector 122 comprises a DEP device 200. As shown, the DEP device 200 can comprise a first electrode 204, a second electrode 210, an electrode activation substrate 208, a power source 212 (e.g., an alternating current (AC) power source), and a light source 220 (which can be the same as or different than the EM source 136). Medium 144 in the flow region 140 and the electrode activation substrate 208 can separate the electrodes 204, 210. Changing patterns of light 222 from the light source 220 can selectively activate and deactivate changing patterns of DEP electrodes at regions 214 of the inner surface 142 of the flow region 140. (Hereinafter the regions 214 are referred to as "electrode regions.")

In the example illustrated in FIG. 2B, a light pattern 222' directed onto the inner surface 142 illuminates the cross-hatched electrode regions 214a in the square pattern shown. The other electrode regions 214 are not illuminated and are hereinafter sometimes referred to as "dark" electrode regions 214. The relative electrical impedance across the electrode activation substrate 208 from each dark electrode region 214 to the second electrode 210 is greater than the relative impedance from the first electrode 204 across the medium 144 in the flow region 140 to the dark electrode region 214. Illuminating an electrode region 214a, however, reduces the relative impedance across the electrode activation substrate 208 from the illuminated electrode region 214a to the second electrode 210 to less than the relative impedance from the first electrode 204 across the medium 144 in the flow region 140 to the illuminated electrode region 214a.

With the power source 212 activated, the foregoing creates an electric field gradient in the medium 144 between illuminated electrode regions 214a and adjacent dark electrode regions 214, which in turn creates local DEP forces that attract or repel nearby micro-objects (not shown) in the medium 144. DEP electrodes that attract or repel micro-objects in the medium 144 can thus be selectively activated and deactivated at many different such electrode regions 214 at the inner surface 142 of the flow region 140 by changing light patterns 222 projected form a light source 220 (e.g., a laser source or other type of light source) into the microfluidic device 200. Whether the DEP forces attract or repel nearby micro-objects can depend on such parameters as the frequency of the power source 212 and the dielectric properties of the medium 144 and/or micro-objects (not shown).

The square pattern 222' of illuminated electrode regions 214a illustrated in FIG. 2B is an example only. Any pattern of the electrode regions 214 can be illuminated by the pattern of light 222 projected into the device 100, and the pattern of illuminated electrode regions 222' can be repeatedly changed by changing the light pattern 222.

In some embodiments, the electrode activation substrate 208 can be a photoconductive material, and the inner surface 142 can be featureless. In such embodiments, the DEP electrodes 214 can be created anywhere and in any pattern on the inner surface 142 of the flow region 140 in accordance with the light pattern 222 (see FIG. 2A). The number and pattern of the electrode regions 214 are thus not fixed but correspond to the light pattern 222. Examples are illustrated in the aforementioned U.S. Pat. No. 7,612,355, in which the un-doped amorphous silicon material 24 shown in the drawings of the foregoing patent can be an example of photoconductive material that can compose the electrode activation substrate 208.

In other embodiments, the electrode activation substrate 208 can comprise a circuit substrate such as a semiconductor material comprising a plurality of doped layers, electrically insulating layers, and electrically conductive layers that form semiconductor integrated circuits such as is known in semiconductor fields. In such embodiments, electric circuit elements can form electrical connections between the electrode regions 214 at the inner surface 142 of the flow region 140 and the second electrode 210 that can be selectively activated and deactivated by the light pattern 222. When not activated, each electrical connection can have high impedance such that the relative impedance from a corresponding electrode region 214 to the second electrode 210 is greater than the relative impedance from the first electrode 204 through the medium 144 to the corresponding electrode region 214. When activated by light in the light pattern 222, however, each electrical connection can have low impedance such that the relative impedance from a corresponding electrode region 214 to the second electrode 210 is less than the relative impedance from the first electrode 204 through the medium 144 to the corresponding electrode region 214, which activates a DEP electrode at the corresponding electrode region 214 as discussed above. DEP electrodes that attract or repel micro-objects (not shown) in the medium 144 can thus be selectively activated and deactivated at many different electrode regions 214 at the inner surface 142 of the flow region 140 by the light pattern 222. Non-limiting examples of such configurations of the electrode activation substrate 208 include the phototransistor-based device illustrated in FIGS. 21 and 22 of U.S. Pat. No. 7,956,339 and the devices 200, 400, 500, and 600 illustrated throughout the drawings in the aforementioned U.S. patent application Ser. No. 14/051,004, filed Oct. 10, 2013.

In some embodiments, the first electrode 204 can be part of a first wall 202 (or cover) of the enclosure 102, and the electrode activation substrate 208 and second electrode 210 can be part of a second wall 206 (or base) of the enclosure 102, generally as illustrated in FIG. 2A. As shown, the flow region 140 can be between the first wall 202 and the second wall 206. The foregoing, however, is but an example. In other embodiments, the first electrode 204 can be part of the second wall 206 and one or both of the electrode activation substrate 208 and/or the second electrode 210 can be part of the first wall 202. As another example, the first electrode 204 can be part of the same wall 202 or 206 as the electrode activation substrate 208 and the second electrode 210. For example, the electrode activation substrate 208 can comprise the first electrode 204 and/or the second electrode 210. Moreover, the light source 220 can alternatively be located below the enclosure 102.

Configured as the DEP device 200 of FIGS. 2A and 2B, the selector 122 can thus select a micro-object (not shown) in the medium 144 in the flow region 140 by projecting a light pattern 222 into the device 200 to activate one or more DEP electrodes at electrode regions 214 of the inner surface 142 of the flow region 140 in a pattern that surrounds and captures the micro-object. The selector 122 can then move the captured micro-object by moving the light pattern 222 relative to the device 200. Alternatively, the device 200 can be moved relative to the light pattern 222.

Although the barriers 154 that define the holding pens 156 are illustrated in FIGS. 1B and 1C and discussed above as physical barriers, the barriers 154 can alternatively be virtual barriers comprising DEP forces activated by the light pattern 222.

The flow controller 124 can be configured to control a flow of the medium 144 in the flow region 140. For example, the flow controller 124 can control the direction and/or velocity of the flow. Non-limiting examples of the flow controller 124 include one or more pumps or fluid actuators. In some embodiments, the flow controller 124 can include additional elements such as one or more sensors (not shown) for sensing, for example, the velocity of the flow of the medium 144 in the flow region 140.

The control module 130 can be configured to receive signals from and control the selector 122, EM source 136, the detector 138, and/or the flow controller 124. As shown, the control module 130 can comprise a controller 132 and a memory 134. In some embodiments, the controller 132 can be a digital electronic controller (e.g., a microprocessor, microcontroller, computer, or the like) configured to operate in accordance with machine readable instructions (e.g., software, firmware, microcode, or the like) stored as non-transitory signals in the memory 134, which can be, for example, a digital electronic, optical, or magnetic memory device. Alternatively, the controller 132 can comprise hardwired digital circuitry and/or analog circuitry or a combination of a digital electronic controller operating in accordance with machine readable instructions and hardwired digital circuitry and/or analog circuitry. The control module 130 can be configured to perform all or any part of any process, function, step, or the like disclosed herein.

The EM source 136 can selectively direct electromagnetic radiation into the enclosure 102. The electromagnetic radiation can include a wavelength that is absorbed by and/or excites a label, such as a chromophore (e.g., a fluorophore). The electromagnetic radiation can comprise a wavelength in the visible or ultraviolet regions of the electromagnetic spectrum. The EM source 136 can be, for example, a laser light source, a light emitting diode (LED), a high intensity discharge lamp, or the like, which can be controlled by the control module 130 to direct light beams at specific target areas inside the flow region 140. The detector 138 can be a mechanism for capturing images (e.g., digital images) of the flow region 140 including, for example, the pens 156, micro-objects (not shown) in the medium 144, and the staging area 172. The detector 138 can also capture images of the export interface 162. Examples of suitable imaging devices that the detector 138 can comprise include digital cameras or photosensors such as charge coupled devices and complementary metal-oxide-semiconductor imagers. Images can be captured with such devices and analyzed (e.g., by the control module 130 and/or a human operator).

In some embodiments, the pens 156 can be shielded from illumination (e.g., by the selector 122, the EM source, and/or the detector 138) or can be only selectively illuminated for brief periods of time. Biological micro-objects 402 (see FIG. 4) can thus be protected from illumination or illumination of the biological micro-objects 402 can be minimized before the biological micro-objects 502 (see FIGS. 5 and 6) are exported.

FIG. 3 illustrates an example process 300 for exporting a group of micro-objects from a micro-fluidic device according to some embodiments. The process 300 can be performed with the micro-fluidic device 100 of FIGS. 1A-1D. The selector 122 can be configured as a DEP device as shown in FIGS. 2A and 2B. The process 300 is not so limited, however, but can be performed with other micro-fluidic devices.

At step 302, the process 300 can move a group of micro-objects from a holding pen in the micro-fluidic device to a staging area. The group can consist of a specific one or more of the micro-objects in the holding pen. FIGS. 4-7 illustrate an example.

As shown in FIG. 4, there can be groups 402 of micro-objects in a plurality of the holding pens 156. For example, the micro-objects can be biological cells, and each group 402 in one of the holding pens 156 can be a clonal colony of cells. As also shown, a flow 404 of the medium 144 can be provided, for example, from the inlet 108 to the outlet 110.

As illustrated in FIG. 5, one of the groups 402 in one of the holding pens 156 can be selected. A particular group 402 and/or holding pen 156 can be identified, for example, from images of the flow region 140 captured by the detector 138 (see FIG. 1A). The selection can be based on the physical characteristics of or an activity associated with the micro-objects in the holding pen 156. Such physical characteristics can include, e.g., the number of micro-objects, their size, their morphology, or the like. Activity associated with the micro-objects can include, e.g., production or presentation of an antigen of interest (such as an antibody, cytokine, growth factor, metabolite, cancer cell marker, or the like), rate of growth, or any combination thereof. In FIG. 5, the selected group 402 is labeled 502. Although the selected group 502 is illustrated as including all of the micro-objects in a pen 156, the selected group 502 can instead include less than all (e.g., 1, 2, 3, 4, 5, or so) of the micro-objects in the group 402 in the pen 156.

In the example shown in FIG. 5, the selected group 502 of micro-objects is trapped with a light trap 504, which can be generated by the selector 122 configured as the DEP device 200 of FIGS. 2A and 2B. For example, the light trap 504 can comprise a contiguous pattern of activated DEP electrodes 214 that enclose the selected group 502. As discussed above, the DEP electrodes 214 can be selectively activated by a pattern 222 of light directed onto the electrode activation substrate 208 (see FIGS. 2A and 2B).

As shown in FIG. 6, the light trap 504 can be moved from the holding pen 156 toward the staging area 172, which also moves the selected group 502 of micro-objects. The light trap 504 can then be moved into the staging area 172. As discussed above, the light trap 504 can be moved by changing the light pattern 222 directed onto the electrode activation substrate 208. Images of the flow region 140 captured by the detector 138 can facilitate selecting, trapping, and moving the group 502 to the staging area 172.

The light trap 504 can be configured to, for example, repel the micro-objects in the medium 144. The light trap 504 can thus keep the micro-objects of the selected group 502 inside the trap 504 and keep all other micro-objects from every other group 402 outside of the trap 504. The light trap 504 can thus prevent both the micro-objects in the selected group 502 from mixing with any other group 402 of micro-objects in the device 100 and any micro-object that is not of the selected group 502 from mixing with group 502 during step 302 of FIG. 3.

As shown in FIG. 7, once the selected group 502 is in the staging area 172, the light trap 504 can be turned off. As shown in FIG. 7, the flow 404 (see FIG. 4) of medium 144 can be turned off so that the micro-objects of the selected group 502 are not flushed from the staging area 172. Alternatively, the light trap 504 can be kept on in the staging area 172 to hold the group 502 in place in the staging area 172 against a flow of medium 144 in the flow region 140. As yet another alternative, the staging area 172 can include physical barriers (not shown) that can hold the group 502 in place against a flow of medium 144 in the flow region 140.

At step 304 of FIG. 3, the process 300 can export the group 502 of micro-objects from the staging area 172. FIGS. 8 and 9 illustrate an example.

As shown in FIG. 8, the cover 166 of the export interface 162 can be removed, and the export device 182 can be inserted into the interface 162 such that the opening 190 in the first end 188 of the export device 182 is in proximity or contact with the passage 174 into the enclosure 102. As shown in FIG. 8, the opening 190 in the first end 188 of the export device 182 can thus be adjacent to the group 502 of micro-objects in the staging area 172.

As shown in FIG. 9, a pressure differential can be created in the export device 182. The micro-objects in the group 502 disposed in the staging area 172 can thus be drawn through the passage 174 into the enclosure 102 and into the interior 186 of the export device 182. The micro-objects of the group 502 can then be collected or otherwise disposed of at the second end 192 of the export device 182. Alternatively, the export device 182 is not a pressure differential generating device or a pressure differential is not created, but another mechanism draws the micro-objects in the group 502 into the export device 182. For example, a flow (not shown) of the medium 140 can be generated that washes the micro-objects in the group 502 from the staging area 172 into the export device 182. Other forces that can be employed to export micro-objects can include gravity and magnetic force. As yet another alternative, a combination of forces can be used to draw the micro-objects in the group 502 into the export device 182, such as a flow of the medium 140 and a pressure differential generated by the export device 182.

Figure 10:
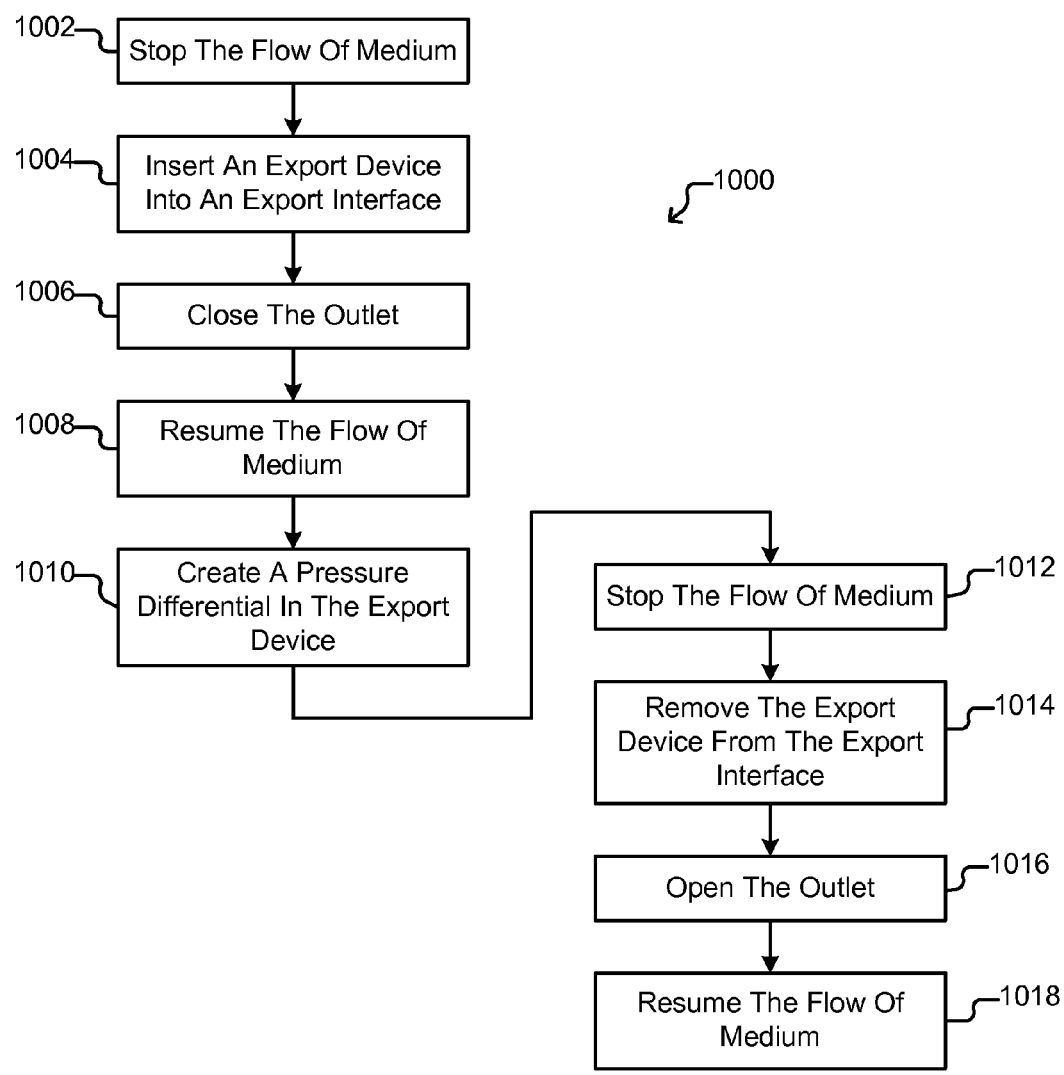
FIG. 10 illustrates an example of a process for exporting a group of micro-objects from the staging area.

FIG. 10 is an example process 1000 by which step 304 of FIG. 3 can be performed. As will be seen, fluid flow can move the micro-objects of the group 502 from the staging area 172 into the export device 182. Such fluid flow can include the flow of the medium 144 in the device 100, a pressure differential by the export device 182, capillary forces by the export device 182, and the like.

At step 1002, the flow 404 (see FIG. 4) of medium 144 in the flow region 140 can be substantially stopped. For example, the control module 130 can cause the flow controller 124 to substantially stop the flow 404. Alternatively, the flow 404 can be slowed at step 1002. At step 1004, the export device 182 can be inserted into the export interface 162, for example, as shown in FIG. 8. At step 1006, the outlet 110 of the micro-fluidic device 100 (see FIGS. 1A-1C) can be closed. Any other exits (not shown) from the enclosure 102 other than the export interface 162 can also be closed.

At step 1008, the flow 404 of medium 144 in the flow region 140 can be resumed. Because the export interface 162 is the only open exit from the enclosure 102, the direction of the flow 404 will be toward and into the export interface 162, and the flow 404 can accordingly sweep the micro-objects of the group 502 from the staging area 172 toward the export device 182.

At step 1010, a pressure differential in the export device 182 can be created, which can draw the micro-objects of the group 502 into the interior 186 of and toward the second end 192 of the export device 182. Alternatively, no pressure differential is created at step 1010, and the flow generated at step 1008 alone (optionally coupled with other forces, such as gravity or magnetic force) draws the micro-objects of the group 502 from the staging area 172 into the export device 182. Some embodiments of the export device 182 thus do not have pressure differential capability.

Once the group 502 of micro-objects has been drawn into the export device 182, the flow 404 of medium 144 can again be substantially stopped or slowed at step 1012, and the export device 182 can be optionally removed from the export interface 162 at step 1014. A pressure differential by the export device 182 can also be turned off at step 1012 or 1014. At step 1016, the outlet 110 of the micro-fluidic device 100 can be opened, and the flow 404 of medium 144 in the flow region 140 can again be resumed at step 1018.

The process 1000 is an example only, and variations are possible. For example, the order of the steps 1002-1018 can, in some instances, be different than shown. In addition, not all steps need to be performed. For example, the export device 182 can be substantially permanently connected to the export interface 162, making it possible to skip steps 1004 and 1014. Similarly, for serial export of micro-objects from different holding pens 156, the outlet 110 can be closed for the first export, but then remain closed for subsequent exporting steps. Accordingly, step 1016 of process 1000 can be skipped, steps 1006 and 1016 of process 1000 can be skipped, steps 1014 and 1016 of process 1000 can be skipped, steps 1004, 1006, 1014, and 1006 of process 1000 can be skipped, or steps 1004, 1006, and 1014 of process 1000 can be skipped.

Referring again to FIG. 3, at step 306, the process 300 can neutralize any un-exported micro-objects at the staging area and the export interface. For a variety of reasons, one or more of the micro-objects of the group 502 might not be exported as part of step 304. For example, a micro-object might unintentionally remain in the staging area 172. As another example, a micro-object might get stuck in the export interface 162.

For a variety of reasons, such un-exported micro-objects at the staging area 172 and export interface 162 might need to be neutralized. For example, in some applications, it can be important to keep the micro-objects in one of the groups 402 from mixing with the micro-objects in another of the groups 402 (see FIG. 4). For example, as noted, each group 402 of micro-objects in the pens 156 can be a clonal colony of biological cells, in which case, it can be important to prevent a living cell that is able to reproduce in one group 402 from mixing with another group because the colony into which the cell is mixed would no longer be clonal. If a micro-object from the group 502 was left in the staging area 172 or the export interface 162, the un-exported micro-object could mix with the next group 402 of micro-objects to be removed from a holding pen 156, moved into the staging area 172, and exported through the export interface 162.

Step 306 can be performed in any of a variety of ways. For example, the detector 138 can capture images of the staging area 172 and the export interface 162, and those images can be inspected for un-exported micro-objects from group 502. The images can be inspected by a human operator and/or utilizing image processing algorithms executed by the control module 130. Any detected micro-objects can be neutralized in any of a variety of possible ways.

For example, un-exported micro-objects at the staging area 172 and/or the export interface 162 can be removed utilizing the selector 122 (e.g., configured as the DEP device 200 of FIGS. 2A and 2B), by flushing the un-exported micro-objects from the staging area 172 and/or export interface 162, or the like. As another example, step 306 can be performed by repeating step 304 one or more times without first moving a new group of micro-objects into the staging area 172 at step 302.

As another example, if the un-exported micro-objects are biological cells, the un-exported biological cells can be neutralized by sterilizing or killing the un-exported cells. FIG. 11 illustrates an example process 1100 for performing step 306 of FIG. 3 when the micro-objects are biological micro-objects such as cells. At step 1102, a treatment can be applied to the staging area 172 and the export interface 162. The treatment can kill or sterilize the biological micro-objects. For example, the treatment can comprise flushing a chemical agent that is fatal to or sterilizes the biological micro-objects through the staging area 172 and export interface 162. As another example, the treatment can comprise directing electromagnetic radiation that is fatal to or sterilizes the biological micro-objects onto the staging area 172 and the export interface 162. For example, the EM source 136 can direct laser beams onto the staging area 172 and the export interface 162. In some embodiments, the detector 138 can capture images of the staging area 172 and/or export interface 162, and such laser beams can be specifically directed at any biological micro-objects detected in the images. Other examples of killing or sterilizing un-exported cells at the staging area 172 or the export interface 162 include the use of electricity, heat or cold, lysis (e.g., with a mechanical cutting micro-instrument), ultrasonic vibrations, or the like.

At step 1104, the process 300 can flush the staging area 172 and export interface 162 to wash away any biological micro-objects in the staging area 172 or export interface 162. For example, the staging area 172 and export interface 162 can be flushed with medium 144. As another example, the staging area 172 and export interface 162 can be flushed with de-ionized water.

At step 1106, the staging area 172 and export interface 162 can be inspected for un-exported biological micro-objects. For example, the detector 138 can capture images of the staging area 172 and export interface 162, which can be inspected for un-exported biological micro-objects as discussed above. If un-exported biological micro-objects are detected, the steps of applying a treatment 1102 and flushing 1104 can be repeated until no un-exported micro-objects are detected at step 1106.

The process 1100 of FIG. 11 is an example only, and variations are contemplated. For example, the inspecting step 1106 can precede the treatment 1102 and flushing 1104 steps, which in some embodiments, are thus performed only if un-exported micro-objects are detected. As another example, the process 1100 can be performed without one or both of the flushing step 1104 or the inspecting step 1106. As yet another example, the process 1100 can be performed without step 1102, such as by flushing un-exported biological micro-objects into a waste receptacle.

Indeed, the devices and processes illustrated in FIGS. 1A-11 are examples, and variations are contemplated. FIGS. 12A-16 illustrate examples of such variations.

Figure 12B:
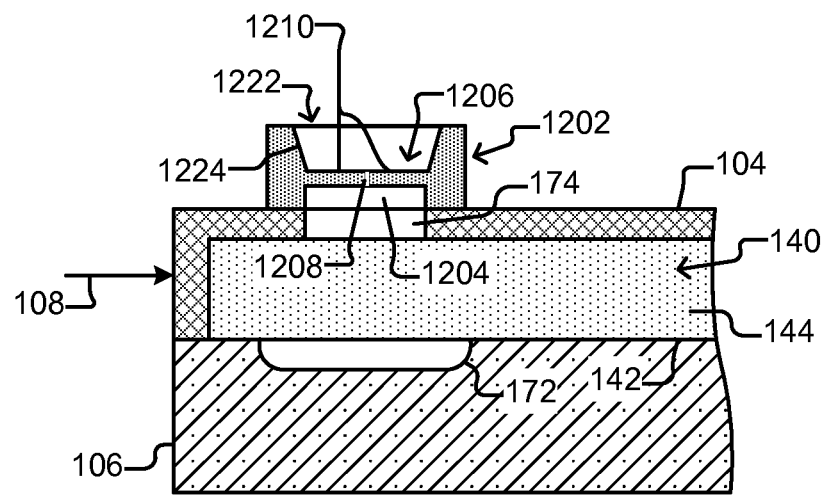
FIG. 12B is a partial, side cross-sectional view of FIG. 12A.
Figure 12C:
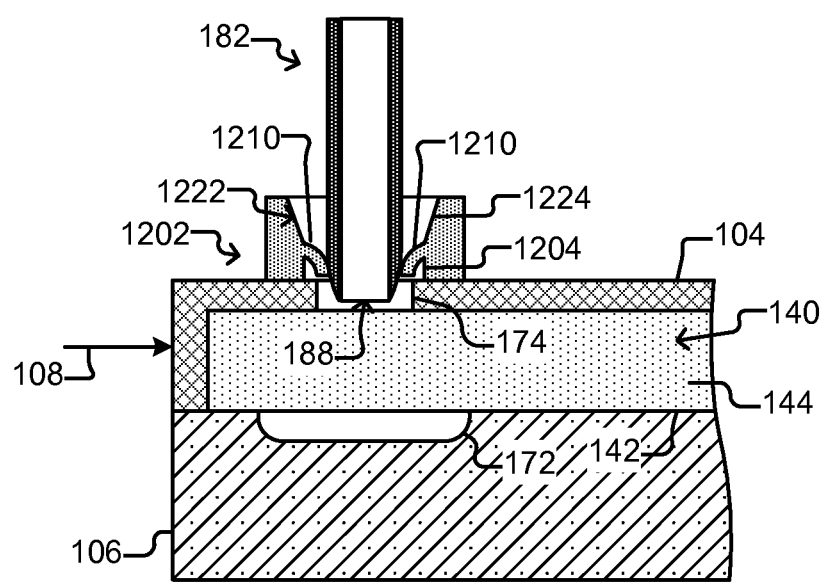
FIG. 12C shows an export device inserted into the export interface of FIGS. 12A and 12B.

FIGS. 12A-12C illustrate another example of an export interface 1202, which can thus replace the export interface 162 in any of the figures or discussions herein. As shown, the export interface 1202 can be disposed on the enclosure 102 over the passage 174. The export interface 1202 can comprise an opening 1204 to the passage 174, a cover 1206 comprising a separation 1208 (e.g., a slit) and flaps 1210, and an entry opening 1222.

As shown in FIG. 12B, the separation 1208 can define and thus separate the flaps 1210. For example, the separation 1208 can comprise one or more slits in the cover 1206. Although the cover 1206 is illustrated as comprising one separation 1208 and two flaps 1210, the cover 1206 can comprise more separations 1208 and flaps 1210. Regardless, the cover 1206 can comprise a flexible, resilient material, and the cover 1206 can be constructed such that internal resilient forces bias the flaps 1210 into proximity or contact so that the cover 1206 covers entirely or substantially entirely the passage 174 through the enclosure 102. The flexibility of the flaps 1210, however, can allow the flaps 1210 to move apart in response to the force of the first end 188 of the export device 182 being pressed against the cover 1206 in the vicinity of the separation 1208. As illustrated in FIG. 12C, the flaps 1210 can move apart, allowing the first end 188 of the export device 182 to be moved into proximity or contact with the passage 174 into the enclosure 102. Although not shown, the resiliency of the flaps 1210 can move the flaps 1210 back into contact such that the cover 1206 covers entirely or substantially entirely the passage 174 as shown in FIG. 12B as the export device 182 is removed from the export interface 1202.

The cover 1206 can thus be closed except when the end 188 of the export device 182 is pressed against and through the cover 1206, in which case the cover opens 1206 to receive the export device 182. As the export device 182 is removed from the cover 1206, the cover 1206 self closes.

The entry 1222 portion of the export interface 1202 can function as a guide that facilitates insertion of the export device 182 into the export interface 1202. As illustrated, the entry 1222 can comprise sloped sidewalls 1224.

Figure 13A:
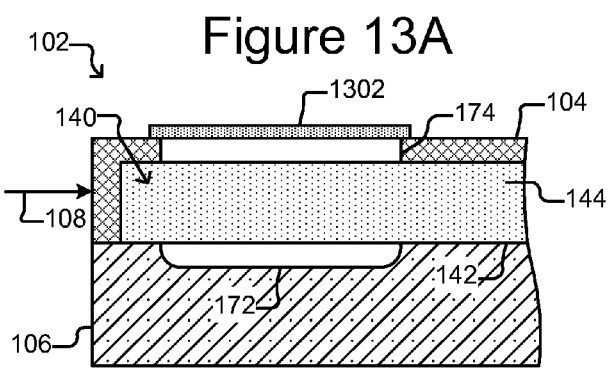
FIG. 13A is a partial, side cross-sectional view of the micro-fluidic device of FIGS. 1A-1C with an embodiment of the export interface that includes a self-healing cover.
Figure 13B:
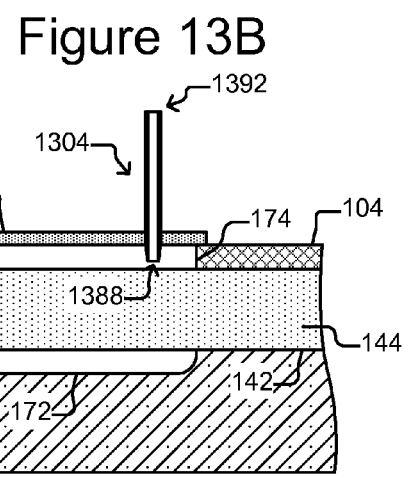
FIG. 13B illustrates an export device in the form of a hypodermic needle inserted into the export interface of FIG. 13A.
Figure 13C:
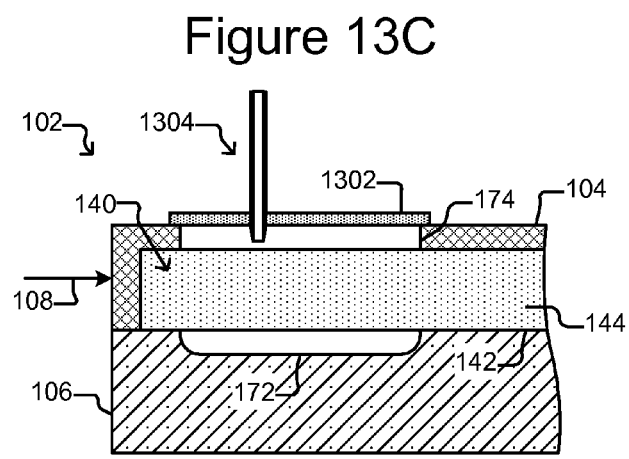
FIG. 13C shows a hypodermic needle inserted into a different part of the export interface of FIG. 13A.

FIGS. 13A-13C illustrate another example of an export interface 1302, which can replace the export interface 162 in any of the figures or discussions herein. As shown, the export interface 1302 can be disposed on the enclosure 102 over the passage 174. The export interface 1302 can comprise a block of material that covers (and thus is a cover 166) entirely the passage 174 as shown in FIG. 13A. The material, however, can be sufficiently pliant to be readily pierced by an export device 1304 as shown in FIG. 13B. In FIG. 13B, the export interface 1302 is pierced by pressing a first end 1388 of an export device 1304, which can be, for example, a hypodermic needle or the like, through the export interface 1302, which thus forms a hole 1306 in the export interface 1302. The export device 1304 can be especially thin but otherwise generally like the export device 182. Thus, while inserted through the export interface 1302 as shown in FIG. 13B, a first end 1388 of the export device 1304 can be in proximity to or contact with the passage 174 into the enclosure 102, and micro-objects (not shown in FIG. 13B) can be drawn into an opening in the first end 1388 of the export device 1304 generally as discussed above with respect to the export device 182. The export device 1304 is thus an example of the export device 182 and can replace the export device 182 in any of the figures or discussions herein. The material of the export interface 1302 can be self-healing so that the hole 1306 made by the export device 182 closes as the export device 1304 is removed from the export interface 1302. Examples of a self-healing material for the export interface 1302 include silicone. As illustrated in FIG. 13C, the export device 1302 can be pierced multiple times in multiple places by the export device 1304. Rather than being a structure separate from the micro-fluidic structure 104, the export interface 1302 can instead be a portion of the micro-fluidic structure 104 immediately adjacent to the staging area 172. In such a case, the structure 104 need not include the passage 174.

Figure 14:
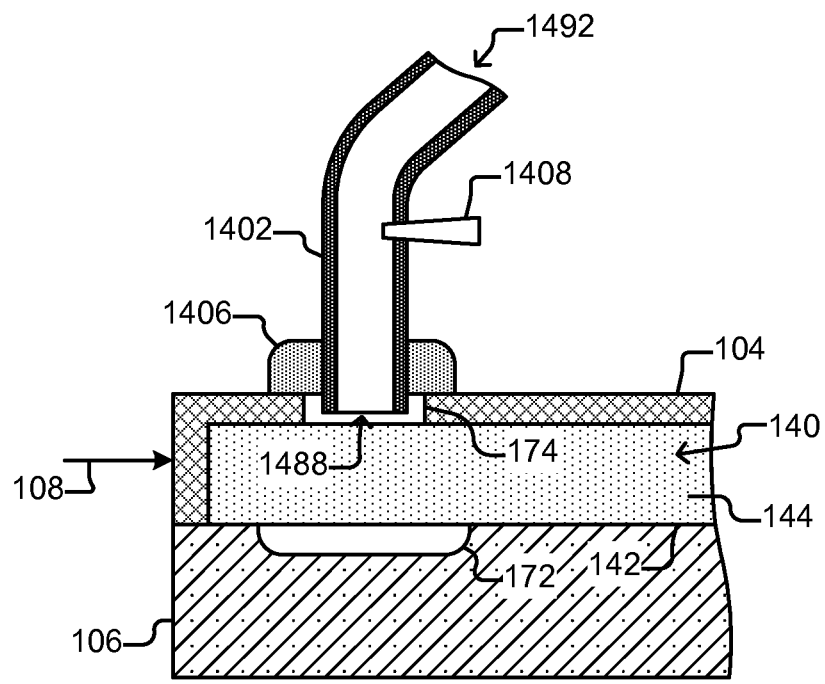
FIG. 14 is a partial, side cross-sectional view of the micro-fluidic device of FIGS. 1A-1C with an embodiment of the export interface that includes an attached tubular export device.

FIG. 14 shows yet another example of an export interface 1406, which can replace the export interface 162 in any of the figures or discussions herein. In FIG. 14, the export interface 1406 can be a fixed attachment mechanism that permanently fixes an access tube 1402 to the enclosure 102 such that a first end 1488 of the tube 1402 is in proximity to or contact with the passage 174 into the enclosure 102. Micro-objects (not shown in FIG. 14) can be drawn into an opening in the first end 1488 of the access tube 1402 generally as discussed above with respect to the export device 182. The access tube 1402 is thus an example of the export device 182 and can replace the export device 182 in any of the figures or discussions herein. As shown, the access tube 1402 can comprise a valve 1408, which can open and close an interior passage in the tube 1402 from the first end 1488 to the second end 1492. The valve 1408 can be, for example, closed except while exporting micro-objects from the staging area 172. However, the access tube 1402 need not comprise a valve 1408, as capillary forces and adjusting the rate of fluid flow through flow region 140 can substitute for valve 1408.

Figure 15A:
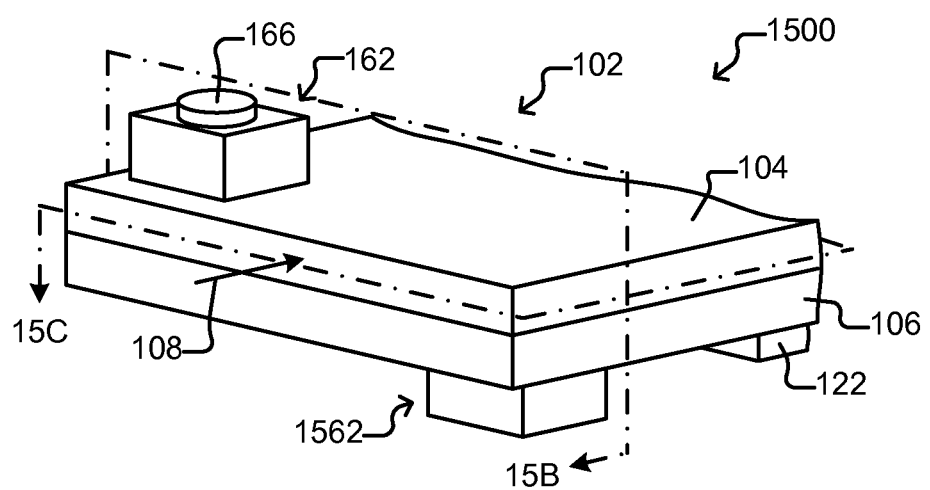
FIG. 15A is a partial, perspective view of a micro-fluidic device that includes a plurality of export interfaces.

FIG. 15A shows a partial perspective view of a micro-fluidic device 1500 that can be an example of a variation of the device 100 of FIGS. 1A-1D. With a few exceptions, the micro-fluidic device 1500 can be like the device 100, and like numbered elements in FIGS. 15A-15C can be the same as in FIGS. 1A-1D.

Figure 15B:
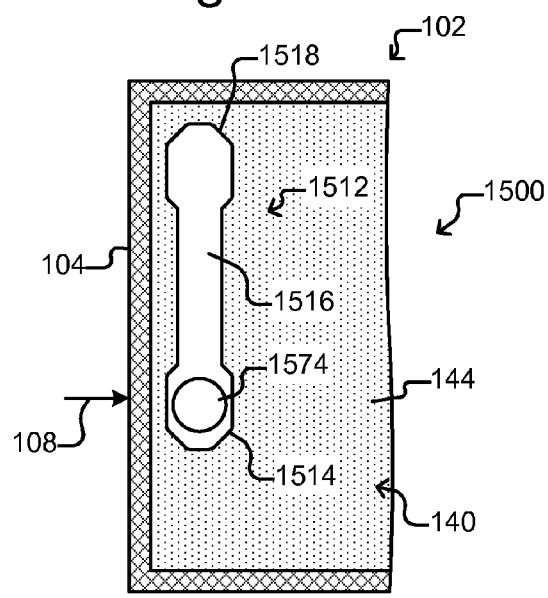
FIG. 15B is top, cross-sectional view of FIG. 15A illustrating a staging area that comprises a middle portion between opposite ends.
Figure 15C:
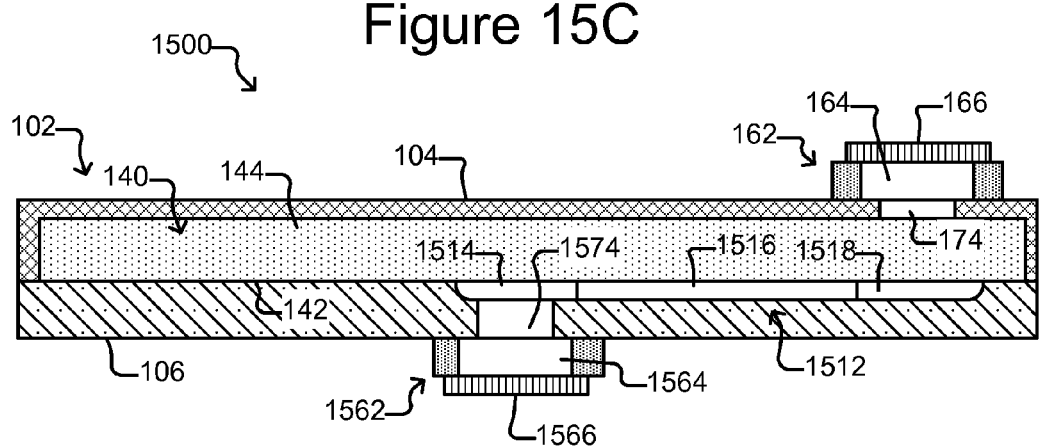
FIG. 15C is a side, cross-sectional view of FIG. 15A.

As shown in FIGS. 15A-15C, the export interface 162 can be a first export interface of the micro-fluidic device 1500, which can also include a second export interface 1562 disposed over a second passage 1574 through the enclosure 102 into the flow region 140. Otherwise, the second export interface 1562 can be similar to the first export interface 162. For example, the second export interface 1562 can comprise an opening 1564 to the passage 1574 and a cover 1566, which can be similar to the opening 164 and cover 166 of the first export interface 162 as discussed above. As also shown, the passages 174, 1574 into the enclosure 102 and thus the export interfaces 162, 1562 can be on opposite sides of the enclosure 102 and need not be aligned one with the other.

The micro-fluidic device 1500 can also have a staging area 1512 that differs from the staging area 172 of the device 100. For example, as shown in FIGS. 15B and 15C, the staging area 1512 can comprise a first end 1518, which can be generally aligned with the passage 174 and thus the first export interface 162; a second end 1514, which can be generally aligned with the passage 1574 and thus the second export interface 1562; and a middle portion 1516 between the ends 1514, 1518. Otherwise, the staging area 1512 can be like the staging area 172 of the device 100 as discussed above. The device 100 can alternatively have a staging area like 1512, which can thus replace the staging area 172 in FIGS. 1A-11 and the discussions above.

The process 300 of FIG. 3 can be performed with the micro-fluidic device 1500 as follows. Step 302 can be performed generally as discussed above. For example, although not visible in the views shown in FIGS. 15A-15C, the device 1500 can include holding pens 156 each of which can hold a group 402 of micro-objects, for example, as shown in FIG. 5. The holding pens 156 can include isolation spaces in which the groups 402 of micro-objects are located. A group of micro-objects can be moved from a holding pen 156 to the staging area or a portion thereof (e.g., the middle portion 1516), generally as illustrated in FIGS. 4-7.

Figure 16:
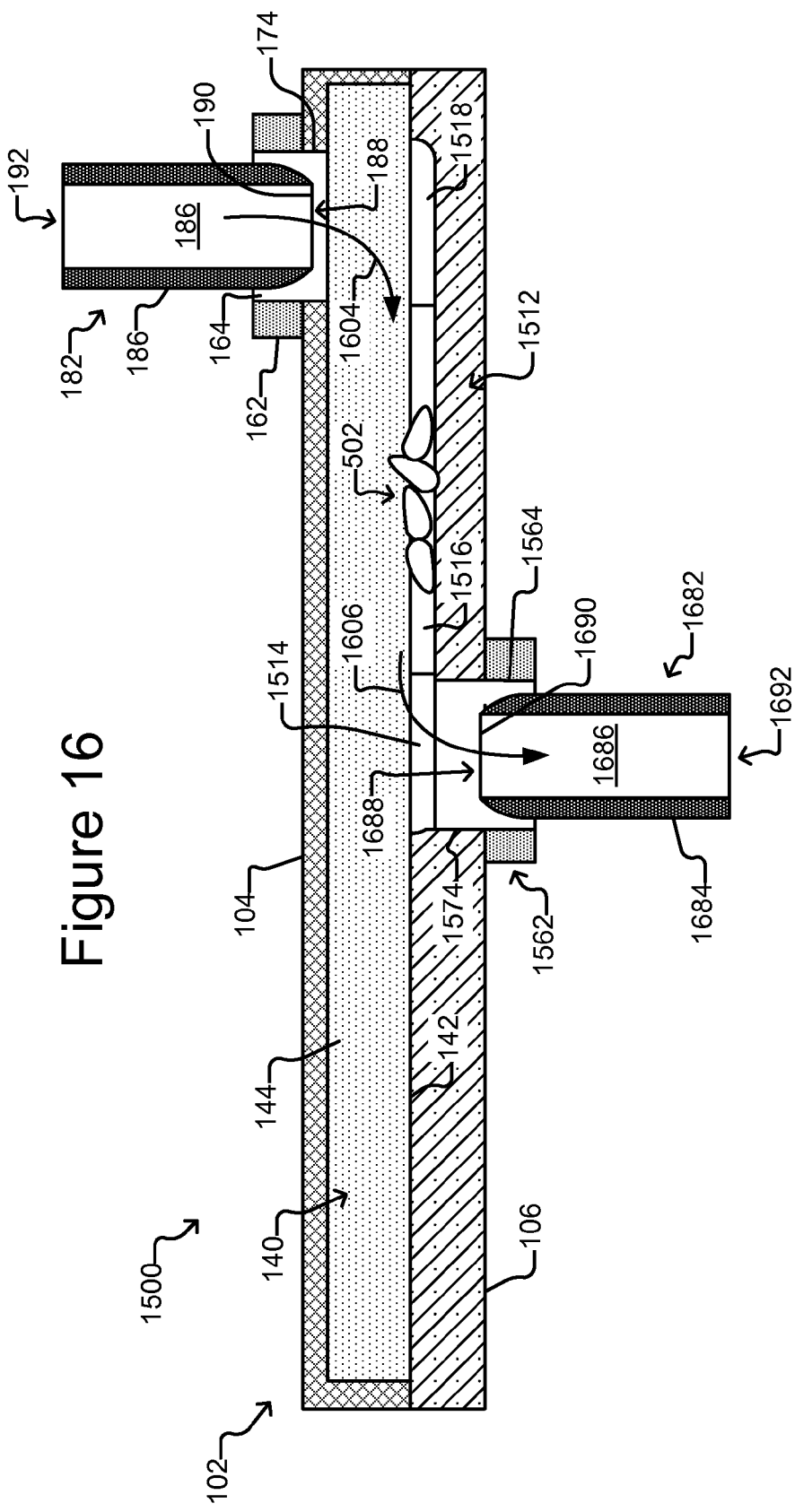
FIG. 16 is a side, cross-sectional view of the micro-fluidic device of FIG. 15A illustrating export devices inserted into the export interfaces.

Step 304 can be performed as illustrated in FIG. 16. The covers 166, 1566 of the export interfaces 162, 1562 can be removed, and a first export device 182 can be inserted into the first interface 162 such that the opening 190 in the first end 188 is in proximity to or contact with the first passage 174 through the enclosure 102. The first export device 182 can be the same as the export device 182 discussed above, and the foregoing can be the same as discussed above.

A second export device 1682 can similarly be inserted into the second interface 1562. The second export device 1682 can be the same as or similar to the first export device 182. The second export device 1682 can thus comprise a hollow tube-like structure comprising a tubular housing 1684 that defines an interior passage 1686 from a first end 1688 to an opposite second end 1692. With the cover 1566 of the second export interface 1562 removed, the second export device 1682 can be inserted into the opening 1564 in the second export interface 1562 such that the first end 1688 is brought into proximity or contact with the second passage 1574 into the enclosure 102.

With the export devices 182, 1682 inserted into the export interfaces 162, 1562 as illustrated in FIG. 16, a flow of liquid (e.g., medium 144) can be generated between the opening 190 of the first export device 182 to the opening 1690 of the second export device 1682, with the flow of liquid passing through the portion of flow region 140 adjacent to staging area 1512. To facilitate such a flow of liquid, a pressure differential can be generated between the opening 190 of the first export device 182 and the opening 1690 of the second export device 1682.

For example, as shown in FIG. 16, a flow of liquid (e.g., medium 144) can be generated from the second end 192 to the first end 188 of the first export device 182. This can create a flow 1604 in the enclosure 102 from the first end 1518 to the second end 1514 of the staging area 1512. The flow 1604 can sweep the selected group 502 of micro-objects from the middle portion 1516 of the staging area 1512 toward the second end 1514 and thus the opening 1690 at the first end 1688 of the second export device 1682. At the same time, a pressure differential can be generated from the first end 1688 to the second end 1692 of the second export device 1682. Such a pressure differential can draw the selected group 502 of micro-objects through the second passage 1574 in the enclosure 102 and into the second export device 1682. The micro-objects of the selected group 502 can then be collected at the second end 1692 of the second export device 1682.

The selected group 502 of micro-objects moved to the staging area 1512 at step 302 of FIG. 3 can thus be exported at step 304. Thereafter, the staging area 1512, the first export interface 162, and/or the second export interface 1562 can be flushed and/or neutralized of un-exported micro-objects at step 306, generally as discussed above.

FIG. 17 illustrates another variation of the device 100 of FIGS. 1A-1D. As shown, the device 1700 of FIG. 17 can comprise a plurality of staging areas 1772 each of which can be like the staging area 172 as discussed above, and the device 1700 can include a plurality of outlets 110a, 110b (which can be as the outlets 110 are described above). In some embodiments, each staging area 1772 can be associated with a single holding pen 156. Otherwise, the device 1700 can be like the device 100 of FIGS. 1A-1D and like numbered elements can be the same.

As illustrated in FIG. 17, a flow 1704 of the medium can be directed to the staging areas 1772. For example, all of the outlets 110 except for outlet 110a can be closed, diverting fluid flow from channel 152 and creating a single flow path 1752 generally from the inlet 108 to the staging areas 1772 and to the only open outlet 110a. Micro-objects (not shown in FIG. 17) can be moved to a staging area 1772 by simply moving the micro-objects from one of the pens 156 into the flow 1704, which can then carry the micro-objects to the staging areas 1772, where the micro-objects (not shown) can be removed through an adjacent export interface (not shown) as discussed above. Alternatively, in some embodiments, micro-objects (not shown in FIG. 17) can be moved from one of the pens 156 to a staging area 1772 and the flow 1704 can carry the micro-objects to and out of the outlet 110a. The outlet 110a can thus function as an export interface. The outlet 110a can be like any of the examples of an outlet 110 discussed above, including a simple hole through the enclosure 102.

FIG. 18 illustrates a variation of the device 1700 of FIG. 17. As shown, the device 1800 of FIG. 18 can be generally the same as the device 1700 (and like numbered elements can be the same) except the device 1800 includes a single barrier 1854 that defines the holding pens 156 and divides channel 152 from flow path 1752. In addition, device 1800 includes a single staging area 1772 (or none at all) located in the flow path 1752. As discussed above with respect to FIG. 17, a flow 1704 of the medium 144 can be created in the flow path 1752 by closing all of the outlets 110 except for the outlet 110a. Micro-objects (not shown in FIG. 18) can be exported from the device 1800 by moving the micro-objects from one of the pens 156 to the staging area 1772, where the micro-objects (not shown) can be removed through an adjacent export interface (not shown) as discussed above. Alternatively, micro-objects (not shown in FIG. 18) can be exported from the device 1800 by moving the micro-objects from one of the pens 156 to the staging area 1772 or (if there is no staging area) into the flow 1704, and flow 1704 can then carry the micro-objects to and out of the outlet 110a. The outlet 110a can be like any of the examples of an outlet 110 discussed above including a simple hole through the enclosure 102.

Figure 19A:
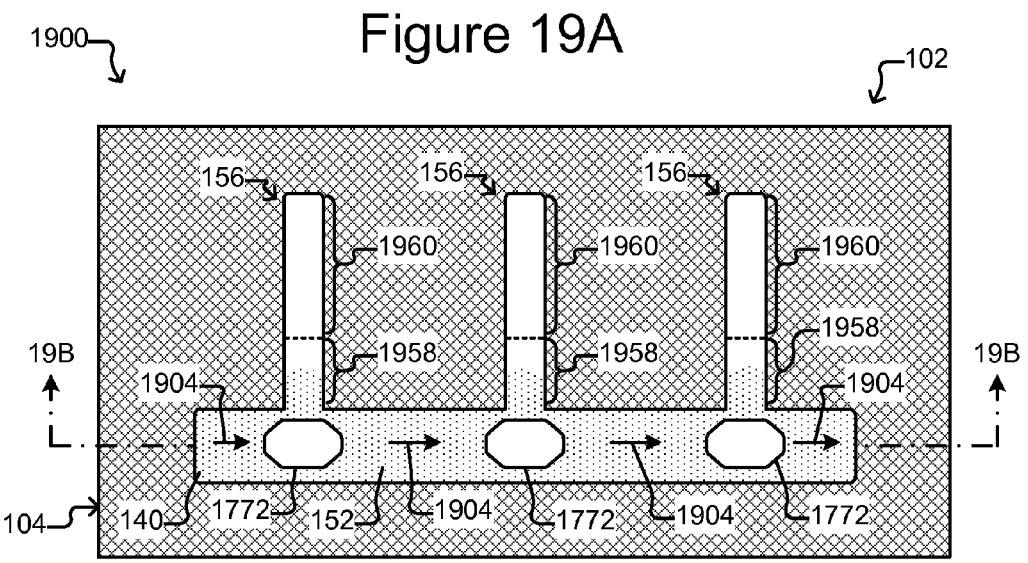
FIG. 19A is a top, cross-sectional view of a micro-fluidic device comprising holding pens with staging areas located in a channel from which the holding pens open, adjacent to the opening to each holding pen.
Figure 19B:
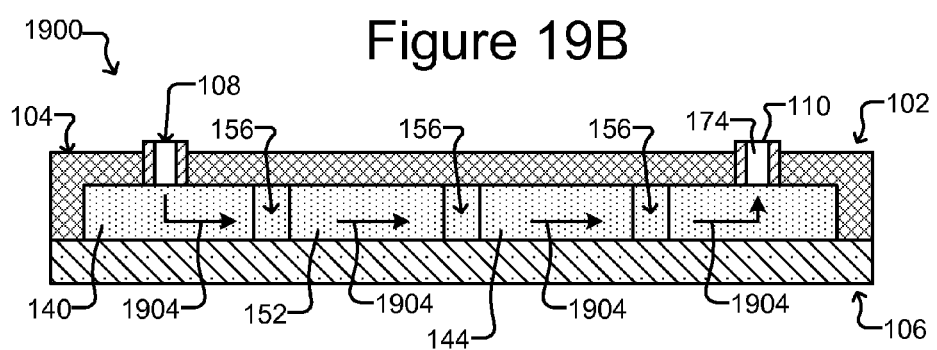
FIG. 19B is a side, cross-sectional view of the microfluidic device of FIG. 19A.

FIGS. 19A-19B illustrate another variation of the device 1700 of FIG. 17. As shown, the device 1900 of FIGS. 19A-19B can be generally the same as the device 1700 (and like numbered elements can be the same) except the device 1900 includes a channel 152 that also functions as flow path 1752. In the embodiment shown, each staging area 1772 is located in the channel 152, adjacent to the opening to a holding pen 156. However, the number of staging areas in device 1900 can be less than the number of holding pens 156 and/or the staging areas need not have specific locations in channel 152 (i.e., any location in channel 152 can be considered a staging area 1772). As shown in FIG. 19B (a side, cross-section of device 1900), the inlet 108 to and/or outlet 110 from flow region 140 can be located above flow region 140, and the outlet can function as an export interface having a passage 174. The outlet 110 can be connected to an export device (not shown), generally in the manner discussed above. Furthermore, the holding pens 156 can have isolation regions 1960 and connection regions 1958, with the isolation regions 1960 fluidically connected to the channel 152 via the connection regions 1958. Micro-objects (not shown in FIGS. 19A-19B) can be exported from the device 1900 by moving the micro-objects from one of the pens 156 to a staging area 1772 in channel 152, and flow 1904 can then carry the micro-objects to the outlet 110 and out into the export device.

FIG. 20 illustrates an example of a process 2000 for exporting micro-objects from the device 1900 of FIGS. 19A-19B. As shown, at step 2002, the process 2000 can create the flow 1904 of medium 144 in the enclosure 102 of the device 1900 directly to the outlet 110. For example, the flow 1904 can flush medium 144 through channel 152 and out the outlet 110. The flush at step 2002 can clear the device 1900 of micro-objects that may be present in channel 152, around the outlet 110 (i.e., export interface), and/or in the export device (not shown). In certain embodiments, the amount of medium 144 flushed through the device 1900 at step 2002 is at least 2 times (e.g., at least 3, 4, 5, 10, 15, 20, 25 times, or more) the combined volume of fluid that the device 1900 and export device are capable of holding. The flushing medium can be flowed into the channel at a rate of about 0.05 to 5.0 µL/sec (e.g., about 0.1 to 2.0, 0.2 to 1.5, 0.5 to 1.0 µL/sec, or about 1.0 to 2.0 µL/sec). The flow 1904 of medium at step 2002 can be continuous, pulsed, periodic, random, intermittent, or reciprocating flow of the liquid, or any combination thereof.

At step 2004, the process 2000 can include slowing or substantially stopping the flow 1904 of medium 144 in channel 152. For example, the flow 1904 of medium 144 in channel 152 can be slowed to a rate of about 0.05 µL/sec or less.

At step 2006, the process 2000 can select a group of micro-objects in one of the holding pens 156 and, at step 2008, move the selected group into the channel 152 (e.g., to a staging area 1772 located adjacent to the opening of the pen 156 or some other region of the channel 152). Although not shown in FIGS. 19A-19B, the holding pens 156 can contain groups of micro-objects 402 as illustrated in FIG. 5. Steps 2006 and 2008 can be performed, for example, as illustrated in FIGS. 5-7 except the selected group 502 is moved into the channel 152 of FIGS. 19A-19B rather than the staging area 172 of FIGS. 5-7. If a light trap (e.g., like light trap 504 in FIGS. 5-7) is used to move the group of micro-objects 502, the light trap can be turned off once the micro-objects 502 are situated in the channel 152.

At step 2010, the flow 1904 of medium 144 in channel 152 can be resumed and the selected group of micro-objects 502 can be carried with the flow 1904 and exported through outlet 110, out into the export device (not shown), and through the distal end of the export device. During step 2010, the flow 1904 of medium 144 in channel 152 can be resumed, for example, at a rate of about 0.05 to 0.25 µL/sec (e.g., about 0.1 to 0.2 µL/sec or about 0.14 to 0.15 µL/sec). The flow 1904 of medium can be continuous, pulsed, periodic, random, intermittent, or reciprocating flow of the liquid, or any combination thereof.

For process 2000 (as well as processes 300 and 1000), the export device can be configured to export medium 144 (or other solution) into a receptacle, such as a test tube, a well in a microtiter plate, or the like. The distal end of the export device (e.g., second end 192 in FIG. 1D or second end 1692 in FIG. 16) can contact the surface of a liquid contained in the receptacle, thereby bringing the volume of exported medium 144 into direct contact with the liquid in the receptacle. Alternatively, the distal end of the export device can contact a bottom or side wall of the receptacle. Such direct contact, whether with the receptacle or a liquid contained in the receptacle, can assist with reducing surface tension that might otherwise tend to keep the volume of the exported medium 144 (or some fraction thereof) associated with the export device.

Step 2010 of process 2000 can include discarding unwanted medium 144 prior to exporting the selected group of micro-objects 502. Once the group of micro-objects 502 has been moved to a staging area 1772 (e.g., the region of the channel 140 located adjacent to the opening of the holding pen 156 from which the selected group of micro-objects 502 was removed (see FIG. 19A)), there will be a "leading volume" of liquid medium 144 that occupies (i) the portion of the channel 140 located between the staging area 1772 and the outlet 110, and (ii) the interior passage of the export device (not shown), between the proximal end (e.g., first end 188 of export device 182) and the distal end (e.g., second end 192 of export device 182). As this leading volume of liquid medium 144 should not contain any micro-objects, it may be desirable to discard it, for example, to a waste receptacle accessible to the second end of the export device. Accordingly, step 2010 can include flowing a volume of liquid medium 144 equivalent to a leading volume through the device 1900, such that the leading volume is discarded, then completing export of the selected group of micro-objects 502. After discarding the leading volume of liquid medium 144, but prior to completing export of the group of micro-objects 502, the flow 1904 of liquid medium 144 in channel 140 can be slowed or substantially stopped for a period of time sufficient to move the distal end of the export device to a receptacle into which the group of micro-objects 502 can be exported.

Once the selected group of micro-objects 502 have been exported, step 2010 can further include neutralizing any un-exported micro-objects that may be stuck in the channel 140, outlet 110, and/or the export device. Any of the neutralizing techniques discussed above can be utilized. For example, the neutralizing technique can comprise or consist of flushing the device 1900, including the export device. Such flushing can constitute step 2002 of a new round of export.

In one variation on process 2000, the liquid medium 144 used at step 2002 to flush the channel 140, the outlet 110, and/or the export device (not shown) and at step 2010 to export the selected group of micro-objects 502 can be replaced with an alternative solution. The alternative solution can be suitable for processing of the group of micro-objects 502 after they have been exported. The solution can be, for example, a solution that doesn't support cell growth, a solution that cells do not tolerate well for long periods of time, or a solution compatible with or useful for assaying biological activity. For example, the solution can be a HEPES buffer, phosphate buffered saline (PBS), osmotically-balanced sugar water, or the like. In this variation on process 2000, step 2010 can include a flushing step with liquid medium 144 such that the alternative solution is washed out of device 1900. Provided that steps 2002 through 2010 are performed rapidly, exposure of the groups of micro-objects 402 (not shown) located in the isolation regions of holding pens 156 to the alternative solution can be limited, thereby substantially mitigating any damaging effect that the alternative solution might otherwise have on the groups of micro-objects 402.

Any of the foregoing steps of process 2000, such as discarding a leading volume of liquid medium 144, or flushing and exporting in a solution different from liquid medium 144, and any of the specific conditions, such as flow rates and the like, can be likewise applied in processes 300 or 1000, as appropriate.

For any of processes 300, 1000, or 2000, the selected group of micro-objects 502 being exported can be exported in a pre-determined volume of medium 144 (or other solution). The volume of medium 144 can depend on the number of micro-objects in the group and how the group of micro-objects 502 is going to be processed after export. Thus, for example, the group of micro-objects 502 can be exported in a volume of medium 144 that is less than 5 µL (e.g., less than 4 µL, 3 µL, 2 µL, 1 µL, 750 nL, 500 nL, 250 nL, 200 nL, 150 nL, 100 nL, 75 nL, 50 nL, or less). Alternatively, the group of micro-objects 502 can be exported in a volume that is about 1 to 10 µL, 5 to 15 µL, 10 to 20 µL, 15 to 25 µL, 20 to 30 µL, 25 to 35 µL, 30 to 40 µL, 35 to 45 µL, 40 to 50 µL, or any range defined by two of the foregoing endpoints. For single cell genomics applications or the like, the group of micro-objects 502 can consist of a single cell and the volume of exported medium 144 that contains the single cell can be relatively small (e.g., less than 5 µL). For cell line development or clonal expansion of cells, the group of micro-objects can include a plurality of cells and the volume of exported medium 144 that contains the plurality of cells can be relatively large (e.g., 5 µL, 10 µL, 25 µL, 50 µL, or more). For assaying activity associated with micro-objects, the group of micro-objects 502 can include one or a plurality of micro-objects and the volume of exported medium 144 that contains the group of micro-objects 502 can be relatively small or relatively large, as appropriate for the particular assay.

To prevent dilution and/or evaporation of the exported volume of medium 144, particularly when the volume of exported medium 144 is small (e.g., 1 µL or less), the volume of exported medium 144 (containing the group of micro-objects) can be exported into a non-aqueous liquid, such as an oil (e.g., mineral oil). Alternatively, the volume of exported medium 144 can be exported into culture medium (e.g., fresh cell growth medium), assay medium (e.g., containing appropriate assay components), or some other solution (e.g., PBS, cell lysis buffer, and the like) suitable for subsequent processing of the micro-objects contained within the volume of exported medium 144.

Figure 21B:
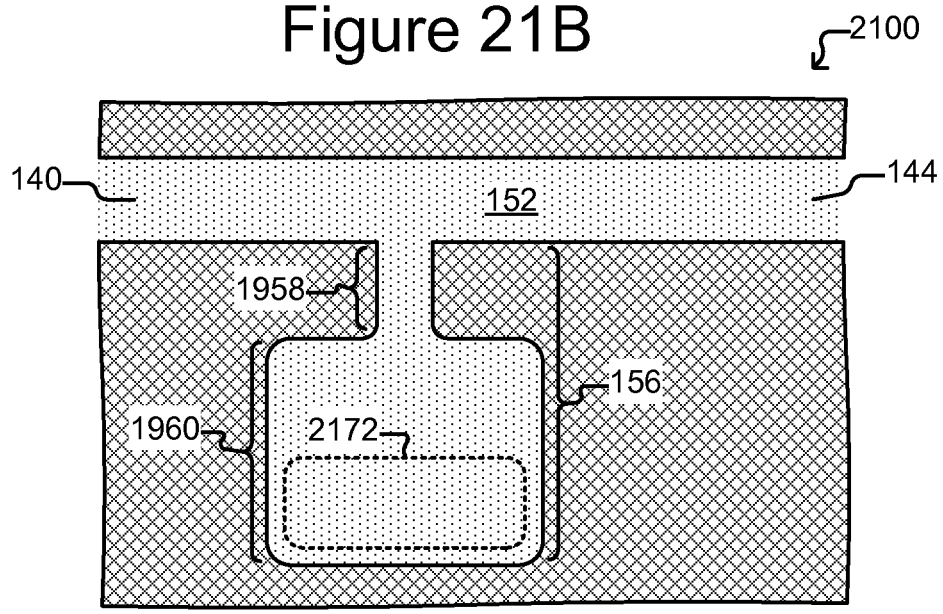
FIG. 21B is a partial, top, cross-sectional view of a micro-fluidic device in which the holding pen includes an isolation region, a portion of which is a staging area.
Figure 21C:
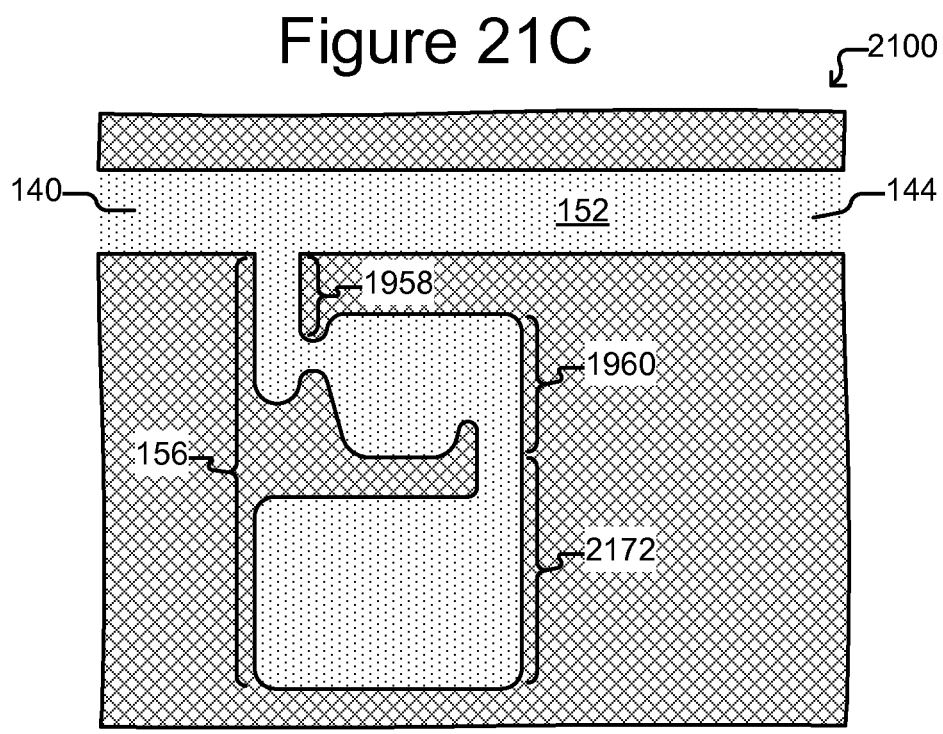
FIG. 21C is a partial, top, cross-sectional view of a holding pen in a microfluidic device in which the holding pen includes an isolation region and a connected staging area.

For any of processes 300, 1000, or 2000, the selected group of micro-objects 502 can be exported individually or in series with other groups of selected micro-objects (i.e., the processes 300, 1000, and 2000 can be repeated). In some embodiments, exporting groups of micro-objects in series involves repeating specific steps of the process, while other steps in the process are not repeated. For example, in process 2000 steps 206 and 208 can be repeated a plurality of times without repeating steps 2002, 2004, and 2010, resulting in a plurality of selected groups of micro-objects 502 being present in channel 140. During export at step 2010, predetermined volumes of liquid medium 144 can be serially exported into different receptacles. By adjusting the predetermined volume of liquid medium 144 such that the volume contains only a single group of selected micro-objects, mixing between the plurality of selected groups of micro-objects can be avoided. FIGS. 21A-21C illustrate additional variations of the devices disclosed herein (e.g., device 100 of FIGS. 1A-1D or device 1900 of FIGS. 19A-19B). As shown, the device 2100 of FIG. 21A can comprise a passage 174 through the micro-fluidic structure 104 and an export interface 1302 in the form of a pierceable cover adjacent to each of the holding pens 156 so that a hypodermic needle 1304 or other such export device can pierce the interface 1302 and remove micro-objects (not shown in FIG. 21A) directly from a pen 156. Each passage 174, each export interface 1302, and the hypodermic needle 1304 can otherwise be the same as like numbered elements in FIGS. 13A-13C. Moreover, the device 2100 can otherwise be like the device 100 of FIGS. 1A-1D or the device 1900 of FIGS. 19A-19B, and like numbered elements can be the same. FIGS. 21B and 21C show different ways in which the export interface 1302 can be adjacent to a holding pen 156. In FIG. 21B, the holding pen 156 includes an isolation region 1960, a portion of which forms a staging area 2172 above which the export interface 1302 can be located. Micro-objects 204 (not shown) located in the staging area 2172 portion of the holding pen 156 are thus accessible for direct export from the holding pen 156. In FIG. 21C, the holding pen 156 includes an isolation region 1960 that is connected (in this case, by means of a passage) to a staging area 2172 above which the export interface 1302 can be located. As a group of micro-objects 402 (not shown), such as a population of cells, multiplies in the isolation region 1960 of the holding pen 156 of FIG. 21C, cells will begin moving into the staging area. Such movement can be achieved, for example, by a force that includes gravity. Again, once micro-objects are present in the staging area 2172, they are accessible for direct export from the holding pen 156.

Rather than an export interface 1302 in the form of a pierceable cover 1302 and an export device in the form of a hypodermic needle 1304 as shown in FIG. 21A, the device 2100 can utilize any export interface and export device illustrated and described herein. For example, the export interface 162 of FIGS. 1A-1D can replace any or all of the export interfaces 1302 in FIG. 21A, and the export device 182 can replace the hypodermic needle 1304. As another example of a variation of the device 2100, rather than being a structure separate from the micro-fluidic structure 104, the export interface 1302 can instead be a portion of the micro-fluidic structure 104 immediately adjacent to a pen. In such a case, the structure 104 need not include passages 174.

Methods of export that involve direct export from a holding pen 156 can be used to export a selected group of micro-objects 502 in a very small volume of fluid medium 144 (or other solution). For example, the export device (such as a hypodermic needle 1304) can have a small volume of air located within the proximal end (i.e., the first end 1388 that gets inserted into/through the export interface 1302) prior to being inserted through the export interface 1302. Upon insertion, the export device can take up (e.g., aspirate up) a pre-determined volume of liquid medium 144 that includes the selected group of micro-objects 502. The export device can then be removed from the export interface 1302 and moved to an appropriate receptacle, whereupon the volume of liquid medium 144 (along with the group of micro-objects 502) taken up by the export device is expelled into the receptacle. The air located within the proximal end of the export device can thus prevent the exported volume of liquid medium 144 from mixing with fluid that would otherwise be present in the export device. In addition, by avoiding an export path that goes through the channel 152, export interface 162, and/or the length of the interior passage of the export device 182, an increase in exported volume due to the selected group of micro-objects 502 spreading out as they travel and/or a loss of micro-objects along the export path can be avoided. Moreover, the export device in this embodiment (e.g., a hypodermic needle 1304) can be readily cleaned and/or un-exported micro-objects can readied for further use by flushing the export device with a solution, such as a cleaning or neutralizing solution. By flushing the solution through the export device and into an external waste receptacle, introduction of potentially harmful chemicals into the microfluidic device (e.g., device 100, 1700, 1800, 1900, or the like) can be avoided.

Any of the steps of the process 300, 1000, 1100, 2000 of FIGS. 3, 10, 11, and 20 can be performed with the export interfaces 1202, 1302, 1406 in FIGS. 12A-12C, 13A and 13B, and 1406 or the outlet 110a of FIG. 17 or 18 in place of the export interface 162 and/or the export interface 1562 in FIGS. 1A-11 and 15A-16. Likewise, any of the steps of the process 300, 1000, 1100, 2000 of FIGS. 3, 10, 11, and 20 can be performed with the export devices 1304, 1402 of FIGS. 13A-14 in place of the export devices 182, 1682 in FIGS. 1A-11 and 16. Similarly, the process 300, 1000, 1100, 2000 of FIGS. 3, 10, 11, and 20 can be performed with the micro-fluidic devices 1500, 1700, 1800, 1900, 2100 of FIGS. 15A-19B and 21A-C rather than the device 100.

Although specific embodiments and applications of the invention have been described in this specification, these embodiments and applications are exemplary only, and many variations are possible. For example, although the passages 174 are illustrated in the drawings as passing through the top of the enclosure 102, the passages 174 can alternatively be through a side or the bottom of the enclosure 102, and the export interfaces 162, 1202, 1302, 1406 (or outlets 110, 110a) can accordingly be on the side or the bottom of the enclosure 102.

What is claimed:

1. A process of exporting micro-objects from a micro-fluidic device having an enclosure which comprises a plurality of holding pens, said processing comprising:
   selecting a group of micro-objects located in a holding pen that is one of said plurality of holding pens inside said enclosure of said micro-fluidic device;
   moving said selected group of micro-objects to a staging area inside said enclosure; and
   exporting ones of said micro-objects of said selected group from said staging area through a passage in said enclosure to a location outside of said enclosure.

2. The process of claim 1, wherein said moving comprises isolating said group of micro-objects from all other micro-objects disposed in said micro-fluidic device.

3. The process of claim 1, wherein each holding pen of said plurality comprises an isolation region configured to hold a plurality of micro-objects.

4. The process of claim 1, wherein each micro-object of said selected group is a biological cell.

5. The process of claim 4, wherein said selected group is a single biological cell.

6. The process of claim 4, wherein said selected group is a clonal population of biological cells.

7. The process of claim 1, wherein:
   said selecting comprises determining that said group of micro-objects has a particular activity or physical characteristic.

8. The process of claim 1, wherein:
   said selecting comprises directing a pattern of light into said micro-fluidic device, wherein said pattern of light surrounds said micro-objects of said selected group and activates DEP forces that trap said micro-objects of said selected group; and
   said moving comprises moving said pattern of light to said staging area, wherein said micro-objects of said selected group remain trapped by said DEP forces activated by said pattern of light as said pattern of light moves to said staging area.

9. The process of claim 1, wherein said staging area is located in a channel defined by said enclosure of said micro-fluidic device.

10. The process of claim 1, wherein said staging area is located within said holding pen.

11. The process of claim 10, wherein moving said selected group of micro-objects to said staging area comprises allowing gravity to attract said group of micro-objects to said staging area.

12. The process of claim 1, wherein said exporting comprises drawing said micro-objects of said selected group from said staging area through said passage in said enclosure by drawing said micro-objects of said selected group through an opening in a proximal end of an export device.

13. The process of claim 12, wherein said drawing comprises generating a pressure differential that draws said micro-objects of said group into said opening at said proximal end of said export device.

14. The process of claim 12, wherein said exporting further comprises inserting said export device into an export interface disposed over said passage in said enclosure, to thereby place said opening at said proximal end of said export device adjacent to said passage.

15. The process of claim 14, wherein:
said export interface comprises a self-closing cover disposed over and covering said passage; and
said inserting comprises opening said cover by pressing said proximal end of said export device against a separation in said cover and moving said proximal end of said export device to be adjacent said passage.

16. The process of claim 14, wherein:
said export interface comprises a self-healing cover disposed over and covering said passage; and
said inserting comprises piercing said cover with said proximal end of said export device and positioning said proximal end of said export device adjacent to said passage.

17. The process of claim 1, wherein said selected group of micro-objects is exported in a medium or other solution having a volume of 1 µL or less.

18. The process of claim 12 further comprising, after said exporting, inspecting said export device for any un-exported micro-objects of said selected group.

19. The process of claim 18 further comprising removing any un-exported ones of said micro-objects from said export device.

20. The process of claim 1, wherein:
said passage in said enclosure is a second passage in said enclosure and is disposed adjacent a second end of said staging area,
said moving comprises moving said selected group to a middle portion of said staging area between said second end and an opposite first end of said staging area, and
said exporting comprises:
flowing a liquid from a first export device through a first passage in said enclosure toward said first end of said staging area and thereby generating a flow from said first end of said staging area to said second end of said staging area, and
drawing said micro-objects of said selected group from said second end of said staging area through said second passage in said enclosure into an opening at a proximal end of a second export device disposed adjacent said second passage.

21. A micro-fluidic apparatus comprising:
an enclosure configured to contain a liquid medium, said enclosure comprising a passage through said enclosure;
a channel disposed inside said enclosure, said channel having a plurality of holding pens which open off of said channel, each holding pen of said plurality configured to hold a group of micro-objects and isolate the group of micro-objects from micro-objects in others of said plurality of holding pens; and
an export interface disposed on said enclosure adjacent said passage, said export interface configured to interface an export device such that an opening in a first end of said export device is positioned adjacent to said passage through said enclosure.

22. The apparatus of claim 21, wherein said enclosure comprises at least one staging area.

23. The apparatus of claim 22, wherein said at least one staging area is located adjacent to said passage through said enclosure.

24. The apparatus of claim 22, wherein said at least one staging area is located in said channel.

25. The apparatus of claim 22, wherein said enclosure comprises a plurality of staging areas, and wherein each holding pen comprises one staging area of said plurality of staging areas.

26. The apparatus of claim 21, wherein said export interface comprises a cover that covers entirely said passage through said enclosure.

27. The apparatus of claim 26, wherein:
said cover comprises a separation dividing said cover into contiguous flaps,
said flaps are biased to contact one another to thereby cover entirely said passage through said enclosure, and
said flaps are sufficiently flexible to move apart to form an opening to receive said first end of said export device in response to a force of said first end of said export device being pressed against said separation.

28. The apparatus of claim 26, wherein said cover comprises a self-healing material that can be pierced by and thus form a hole for receiving said export device but self-heals and thereby closes said hole when said export device is removed from said material.

29. The apparatus of claim 21 further comprising means for trapping a group of said micro-objects in any one of said plurality of holding pens and moving said trapped group of micro-objects to said at least one staging area.

* * * * *